United States Patent
Kubacki et al.

(10) Patent No.: US 12,108,959 B2
(45) Date of Patent: Oct. 8, 2024

(54) PREPARING A TIBIA FOR RECEIVING TIBIAL IMPLANT COMPONENT OF A REPLACEMENT ANKLE

(71) Applicant: WRIGHT MEDICAL TECHNOLOGY, INC., Memphis, TN (US)

(72) Inventors: Meghan Kubacki, Memphis, TN (US); Ramon Luna, Arlington, TN (US); Terrance W. Strohkirch, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 662 days.

(21) Appl. No.: 17/424,416

(22) PCT Filed: Jan. 28, 2020

(86) PCT No.: PCT/US2020/015373
§ 371 (c)(1),
(2) Date: Jul. 20, 2021

(87) PCT Pub. No.: WO2020/242542
PCT Pub. Date: Dec. 3, 2020

(65) Prior Publication Data
US 2022/0087693 A1    Mar. 24, 2022

Related U.S. Application Data

(60) Provisional application No. 62/853,818, filed on May 29, 2019.

(51) Int. Cl.
*A61B 17/16* (2006.01)
*A61B 17/17* (2006.01)
(Continued)

(52) U.S. Cl.
CPC ...... *A61B 17/1682* (2013.01); *A61B 17/1717* (2013.01); *A61B 17/1775* (2016.11);
(Continued)

(58) Field of Classification Search
CPC ............ A61B 17/1682; A61B 17/1775; A61B 17/1717; A61B 2017/564; A61F 2/4606; A61F 2002/4205; A61F 2002/4207
See application file for complete search history.

(56) References Cited

U.S. PATENT DOCUMENTS 3,314,420 A    4/1967  Smith et al.
3,605,123 A    9/1971  Hahn
(Continued)

FOREIGN PATENT DOCUMENTS

AU    2019261830    11/2021
CN    1662186        8/2005
(Continued)

OTHER PUBLICATIONS

Non-Final Office Action issued in connection with Japanese Patent Application No. 2023024381, Jan. 16, 2024, 7 pages.
(Continued)

*Primary Examiner* — Sameh R Boles
(74) *Attorney, Agent, or Firm* — DUANE MORRIS LLP

(57) ABSTRACT

Disclosed is are various methods of preparing a tibial intramedullary canal for receiving a tibial implant, methods of preparing a talus for receiving a talar implant, and some examples of a power driver adapter that can be used to carry out the preparation of the tibial intramedullary canal.

10 Claims, 23 Drawing Sheets

(51) Int. Cl.
  *A61F 2/46* (2006.01)
  *A61B 17/56* (2006.01)
  *A61F 2/42* (2006.01)

(52) U.S. Cl.
  CPC ...... *A61F 2/4606* (2013.01); *A61B 2017/564* (2013.01); *A61F 2002/4205* (2013.01); *A61F 2002/4207* (2013.01)

(56) References Cited

U.S. PATENT DOCUMENTS

| | | |
|---|---|---|
| 3,708,883 A | 1/1973 | Flander |
| 3,798,679 A | 3/1974 | Ewald |
| 3,808,606 A | 5/1974 | Tronzo |
| 3,843,975 A | 10/1974 | Tronzo |
| 3,855,638 A | 12/1974 | Pilliar |
| 3,938,198 A | 2/1976 | Kahn et al. |
| 3,987,499 A | 10/1976 | Scharbach et al. |
| 4,052,753 A | 10/1977 | Dedo |
| 4,055,862 A | 11/1977 | Farling |
| 4,085,466 A | 4/1978 | Goodfellow et al. |
| 4,098,626 A | 7/1978 | Graham et al. |
| 4,203,444 A | 5/1980 | Bonnell et al. |
| 4,213,816 A | 7/1980 | Morris |
| 4,340,978 A | 7/1982 | Buechel et al. |
| 4,368,040 A | 1/1983 | Weissman |
| 4,436,684 A | 3/1984 | White |
| 4,501,266 A | 2/1985 | McDaniel |
| 4,502,161 A | 3/1985 | Wall |
| 4,578,806 A | 3/1986 | Grass et al. |
| 4,586,496 A | 5/1986 | Keller |
| 4,594,380 A | 6/1986 | Chapin et al. |
| 4,601,290 A | 7/1986 | Effron et al. |
| 4,609,551 A | 9/1986 | Caplan et al. |
| 4,627,853 A | 12/1986 | Campbell et al. |
| 4,680,994 A | 7/1987 | Singleton |
| 4,703,751 A | 11/1987 | Pohl |
| 4,704,686 A | 11/1987 | Aldinger |
| 4,715,860 A | 12/1987 | Amstutz et al. |
| 4,721,104 A | 1/1988 | Kaufman et al. |
| 4,759,350 A | 7/1988 | Dunn et al. |
| 4,769,040 A | 9/1988 | Wevers |
| 4,841,975 A | 6/1989 | Woolson |
| 4,846,835 A | 7/1989 | Grande |
| 4,865,607 A | 9/1989 | Witzel et al. |
| 4,878,917 A | 11/1989 | Rybicki et al. |
| 4,880,429 A | 11/1989 | Stone |
| 4,936,862 A | 6/1990 | Walker et al. |
| 4,979,949 A | 12/1990 | Matsen, III et al. |
| 5,002,547 A | 3/1991 | Poggie |
| 5,041,138 A | 8/1991 | Vacanti et al. |
| 5,059,216 A | 10/1991 | Winters |
| 5,063,918 A | 11/1991 | Guhl |
| 5,067,964 A | 11/1991 | Richmond et al. |
| 5,122,144 A | 6/1992 | Bert et al. |
| 5,129,908 A | 7/1992 | Petersen |
| 5,133,759 A | 7/1992 | Turner |
| 5,154,717 A | 10/1992 | Matsen, III et al. |
| 5,162,430 A | 11/1992 | Rhee et al. |
| 5,171,322 A | 12/1992 | Kenny |
| 5,197,985 A | 3/1993 | Caplan et al. |
| 5,206,023 A | 4/1993 | Hunziker |
| 5,226,914 A | 7/1993 | Caplan et al. |
| 5,234,433 A | 8/1993 | Bert et al. |
| 5,250,050 A | 10/1993 | Poggie et al. |
| 5,258,032 A | 10/1993 | Bertin |
| 5,270,300 A | 12/1993 | Hunziker |
| 5,288,797 A | 2/1994 | Khalil et al. |
| 5,303,148 A | 4/1994 | Mattson et al. |
| 5,306,311 A | 4/1994 | Stone et al. |
| 5,314,482 A | 5/1994 | Goodfellow et al. |
| 5,344,459 A | 9/1994 | Swartz |
| 5,360,446 A | 11/1994 | Kennedy |
| 5,365,996 A | 11/1994 | Crook |
| 5,368,858 A | 11/1994 | Hunziker |
| 5,370,692 A | 12/1994 | Fink et al. |
| 5,380,332 A | 1/1995 | Ferrante |
| 5,387,216 A | 2/1995 | Thornhill et al. |
| 5,454,816 A | 10/1995 | Ashby |
| 5,462,550 A | 10/1995 | Dietz et al. |
| 5,468,787 A | 11/1995 | Braden et al. |
| 5,474,559 A | 12/1995 | Bertin et al. |
| 5,478,739 A | 12/1995 | Slivka et al. |
| 5,486,180 A | 1/1996 | Dietz et al. |
| 5,501,687 A | 3/1996 | Willert et al. |
| 5,503,162 A | 4/1996 | Athanasiou et al. |
| 5,520,695 A | 5/1996 | Luckman |
| 5,523,843 A | 6/1996 | Yamane et al. |
| 5,540,696 A | 7/1996 | Booth, Jr. et al. |
| 5,542,947 A | 8/1996 | Treacy |
| 5,554,190 A | 9/1996 | Draenert |
| 5,556,432 A | 9/1996 | Kubein-Meesenburg et al. |
| 5,571,205 A | 11/1996 | James |
| 5,575,793 A | 11/1996 | Carls et al. |
| 5,578,037 A | 11/1996 | Sanders et al. |
| 5,593,450 A | 1/1997 | Scott et al. |
| 5,597,379 A | 1/1997 | Haines et al. |
| 5,601,563 A | 2/1997 | Burke et al. |
| 5,613,970 A | 3/1997 | Houston et al. |
| 5,616,146 A | 4/1997 | Murray |
| 5,630,820 A | 5/1997 | Todd |
| 5,632,745 A | 7/1997 | Schwartz |
| 5,645,604 A | 7/1997 | Schneider et al. |
| 5,658,290 A | 8/1997 | Techeira |
| 5,649,929 A | 9/1997 | Callaway |
| 5,671,741 A | 9/1997 | Lang et al. |
| 5,682,886 A | 11/1997 | Delp et al. |
| 5,683,466 A | 11/1997 | Vitale |
| 5,684,562 A | 11/1997 | Fujieda |
| 5,688,282 A | 11/1997 | Baron et al. |
| 5,728,162 A | 3/1998 | Eckhoff |
| 5,735,277 A | 4/1998 | Schuster |
| 5,749,874 A | 5/1998 | Schwartz |
| 5,749,876 A | 5/1998 | Duvillier et al. |
| 5,765,561 A | 6/1998 | Chen et al. |
| 5,768,134 A | 6/1998 | Swaelens et al. |
| 5,769,899 A | 6/1998 | Schwartz et al. |
| 5,782,842 A | 7/1998 | Kloess et al. |
| 5,786,217 A | 7/1998 | Tuba et al. |
| 5,798,924 A | 8/1998 | Eufinger et al. |
| 5,800,438 A | 9/1998 | Tuke et al. |
| 5,824,083 A | 10/1998 | Draenert |
| 5,827,289 A | 10/1998 | Reiley et al. |
| 5,830,216 A | 11/1998 | Insall et al. |
| 5,835,619 A | 11/1998 | Morimoto et al. |
| 5,842,477 A | 12/1998 | Naughton et al. |
| 5,847,804 A | 12/1998 | Sarver et al. |
| 5,853,746 A | 12/1998 | Hunziker |
| 5,860,981 A | 1/1999 | Bertin et al. |
| 5,871,018 A | 2/1999 | Delp et al. |
| 5,871,542 A | 2/1999 | Goodfellow et al. |
| 5,871,546 A | 2/1999 | Colleran et al. |
| 5,879,390 A | 3/1999 | Kubein-Meesenburg et al. |
| 5,880,976 A | 3/1999 | DiGioia, III et al. |
| 5,885,296 A | 3/1999 | Masini |
| 5,885,297 A | 3/1999 | Matsen, III |
| 5,885,298 A | 3/1999 | Herrington et al. |
| 5,897,559 A | 4/1999 | Masini |
| 5,899,859 A | 5/1999 | Votruba et al. |
| 5,900,245 A | 5/1999 | Sawhney et al. |
| 5,906,934 A | 5/1999 | Grande et al. |
| 5,910,143 A | 6/1999 | Cripe et al. |
| 5,911,723 A | 6/1999 | Ashby et al. |
| 5,916,220 A | 6/1999 | Masini |
| 5,939,323 A | 8/1999 | Valentini et al. |
| 5,951,475 A | 9/1999 | Gueziec et al. |
| 5,961,523 A | 10/1999 | Masini |
| 5,968,051 A | 10/1999 | Luckman et al. |
| 5,972,385 A | 10/1999 | Liu et al. |
| 5,995,738 A | 11/1999 | DiGioia, III et al. |
| 6,001,895 A | 12/1999 | Harvey et al. |
| 6,002,859 A | 12/1999 | DiGioia, III et al. |
| 6,006,126 A | 12/1999 | Cosman |
| 6,007,537 A | 12/1999 | Burkinshaw et al. |

(56) References Cited

U.S. PATENT DOCUMENTS

| | | |
|---|---|---|
| 6,010,509 A | 1/2000 | Delgado et al. |
| 6,013,081 A | 1/2000 | Burkinshaw et al. |
| 6,013,103 A | 1/2000 | Kaufman et al. |
| 6,046,379 A | 4/2000 | Stone et al. |
| 6,056,754 A | 5/2000 | Haines et al. |
| 6,056,756 A | 5/2000 | Eng et al. |
| 6,057,927 A | 5/2000 | Levesque et al. |
| 6,077,270 A | 6/2000 | Katz |
| 6,082,364 A | 7/2000 | Balian et al. |
| 6,090,144 A | 7/2000 | Letot et al. |
| 6,093,204 A | 7/2000 | Stone |
| 6,096,043 A | 8/2000 | Techiera et al. |
| 6,102,916 A | 8/2000 | Masini |
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |
| 6,251,143 B1 | 6/2001 | Schwartz et al. |
| 6,254,639 B1 | 7/2001 | Peckitt |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,327,491 B1 | 12/2001 | Franklin et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,409,767 B1 | 6/2002 | Perice et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,927 B1 | 10/2002 | Franklin et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,738,657 B1 | 5/2004 | Franklin et al. |
| 6,905,514 B2 | 6/2005 | Carignan et al. |
| 6,916,341 B2 | 7/2005 | Rolston |
| 6,928,742 B2 | 8/2005 | Broers et al. |
| 6,932,842 B1 | 8/2005 | Litschko et al. |
| 6,942,667 B1 | 9/2005 | Song |
| 6,944,518 B2 | 9/2005 | Roose |
| 6,969,393 B2 | 11/2005 | Pinczewski et al. |
| 6,980,849 B2 | 12/2005 | Sasso |
| 6,988,015 B1 | 1/2006 | Schopf et al. |
| 6,993,374 B2 | 1/2006 | Sasso |
| 7,008,430 B2 | 3/2006 | Dong et al. |
| 7,058,439 B2 | 6/2006 | Eaton et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,184,814 B2 | 2/2007 | Lang et al. |
| 7,201,762 B2 | 4/2007 | Green, Jr. et al. |
| 7,217,276 B2 | 5/2007 | Henderson et al. |
| 7,239,908 B1 | 7/2007 | Alexander et al. |
| 7,245,697 B2 | 7/2007 | Lang |
| 7,250,055 B1 | 7/2007 | Vanderwalle |
| 7,282,054 B2 | 10/2007 | Steffensmeier et al. |
| 7,292,674 B2 | 11/2007 | Lang |
| 7,347,690 B2 | 3/2008 | Jordan et al. |
| 7,364,581 B2 | 4/2008 | Michalowicz |
| 7,377,924 B2 | 5/2008 | Raistrick et al. |
| 7,379,529 B2 | 5/2008 | Lang |
| 7,467,892 B2 | 12/2008 | Lang et al. |
| 7,468,075 B2 | 12/2008 | Lang et al. |
| 7,534,246 B2 | 5/2009 | Reiley et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,881,768 B2 | 2/2011 | Lang et al. |
| 7,914,533 B2 | 3/2011 | Nelson et al. |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,592 B2 | 2/2012 | Burdulis, Jr. et al. |
| RE43,282 E | 3/2012 | Alexander et al. |
| 8,430,879 B2 | 4/2013 | Stoneburner et al. |
| 8,496,663 B2 | 7/2013 | White et al. |
| 8,535,319 B2 | 9/2013 | Ball |
| 8,579,980 B2 | 11/2013 | Delurio et al. |
| 8,636,744 B2 | 1/2014 | Tochigi et al. |
| 8,715,362 B2 | 5/2014 | Reiley et al. |
| 8,808,297 B2 | 8/2014 | Stemniski |
| 8,808,303 B2 | 8/2014 | Stemniski |
| 9,005,255 B2 | 4/2015 | Lewis et al. |
| 9,017,334 B2 | 4/2015 | Carroll et al. |
| 9,125,674 B2 | 9/2015 | White et al. |
| 9,128,627 B1 | 9/2015 | Bachu et al. |
| 9,259,250 B2 | 2/2016 | Saravia et al. |
| 9,265,511 B2 | 2/2016 | White et al. |
| 9,402,640 B2 | 8/2016 | Stemniski et al. |
| 9,480,490 B2 | 11/2016 | Metzger et al. |
| 9,672,607 B2 | 6/2017 | Demri et al. |
| 9,675,365 B2 | 6/2017 | Lancianese et al. |
| 10,105,168 B2 | 10/2018 | Blau |
| 10,130,430 B2 | 11/2018 | Kao et al. |
| 10,390,842 B2 | 8/2019 | Sander |
| 10,413,308 B2 | 9/2019 | Stemniski et al. |
| 10,433,911 B2 | 10/2019 | Wang et al. |
| 10,456,179 B2 | 10/2019 | Luna et al. |
| 10,667,867 B2 | 6/2020 | Ashish et al. |
| 10,835,265 B2 | 11/2020 | White et al. |
| 10,835,266 B2 | 11/2020 | White et al. |
| 11,134,964 B2 | 10/2021 | Free et al. |

(56) References Cited

U.S. PATENT DOCUMENTS

| | | |
|---|---|---|
| 11,147,627 B2 | 10/2021 | Gangwar et al. |
| 11,172,945 B1 | 11/2021 | Lian |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geisllich et al. |
| 2002/0029038 A1 | 3/2002 | Haines |
| 2002/0045940 A1 | 4/2002 | Giannelli et al. |
| 2002/0055744 A1 | 5/2002 | Reiley |
| 2002/0059049 A1 | 5/2002 | Bradbury et al. |
| 2002/0068979 A1 | 6/2002 | Brown et al. |
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0123817 A1 | 9/2002 | Clasbrummel et al. |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |
| 2002/0156150 A1 | 10/2002 | Asculai et al. |
| 2002/0156479 A1 | 10/2002 | Schulzki et al. |
| 2002/0173852 A1 | 11/2002 | Felt et al. |
| 2002/0183850 A1 | 12/2002 | Felt et al. |
| 2002/0198531 A1 | 12/2002 | Millard et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0225457 A1 | 12/2003 | Justin et al. |
| 2003/0236521 A1 | 12/2003 | Brown et al. |
| 2003/0236526 A1 | 12/2003 | Van Hoeck et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193268 A1 | 9/2004 | Hazebrouck et al. |
| 2004/0193280 A1 | 9/2004 | Webster et al. |
| 2004/0199166 A1 | 10/2004 | Schmieding et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0049603 A1 | 3/2005 | Calton et al. |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0187555 A1 | 8/2005 | Biedermann et al. |
| 2005/0192588 A1 | 9/2005 | Garcia |
| 2005/0216305 A1 | 9/2005 | Funderud |
| 2005/0234461 A1 | 10/2005 | Burdulis et al. |
| 2005/0267584 A1 | 12/2005 | Burdulis et al. |
| 2005/0288792 A1 | 12/2005 | Landes et al. |
| 2006/0052795 A1 | 3/2006 | Burdulis et al. |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0129808 A1 | 6/2007 | Justin et al. |
| 2007/0150065 A1 | 6/2007 | Angibaud |
| 2007/0162025 A1 | 7/2007 | Tornier et al. |
| 2007/0198022 A1 | 8/2007 | Lang et al. |
| 2007/0203430 A1 | 8/2007 | Lang et al. |
| 2007/0203455 A1 | 8/2007 | Tremaglio et al. |
| 2007/0233128 A1 | 10/2007 | Schmieding et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang et al. |
| 2008/0031412 A1 | 2/2008 | Delfosse et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0195109 A1 | 8/2008 | Hunter et al. |
| 2008/0195216 A1 | 8/2008 | Lang |
| 2008/0219412 A1 | 9/2008 | Lang |
| 2008/0243127 A1 | 10/2008 | Lang |
| 2008/0255565 A1 | 10/2008 | Fletcher |
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2008/0287953 A1 | 11/2008 | Sers |
| 2008/0288079 A1 | 11/2008 | Leibel |
| 2008/0306605 A1 | 12/2008 | Hasselman |
| 2009/0024131 A1 | 1/2009 | Metzger et al. |
| 2009/0043310 A1 | 2/2009 | Rasmussen |
| 2009/0076371 A1 | 3/2009 | Lang et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0149964 A1 | 6/2009 | May et al. |
| 2009/0198244 A1 | 6/2009 | Liebl |
| 2009/0204115 A1 | 8/2009 | Dees et al. |
| 2009/0222014 A1 | 9/2009 | Bojarski et al. |
| 2009/0307893 A1 | 12/2009 | Bojarski et al. |
| 2010/0057133 A1 | 3/2010 | Simon |
| 2010/0076441 A1 | 3/2010 | May et al. |
| 2010/0160917 A1 | 6/2010 | Fitz et al. |
| 2010/0262150 A1 | 10/2010 | Lian |
| 2010/0274251 A1 | 10/2010 | Ranft |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2010/0331847 A1 | 12/2010 | Wilkinson et al. |
| 2011/0066193 A1 | 3/2011 | Lang et al. |
| 2011/0071581 A1 | 3/2011 | Lang et al. |
| 2011/0137422 A1 | 6/2011 | Wilkes |
| 2011/0213368 A1 | 9/2011 | Fitz et al. |
| 2011/0213373 A1 | 9/2011 | Fitz et al. |
| 2011/0213374 A1 | 9/2011 | Fitz et al. |

(56) References Cited

U.S. PATENT DOCUMENTS

| | | | |
|---|---|---|---|
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218542 A1 | 9/2011 | Lian et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0010719 A1 | 1/2012 | Reiley |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0083892 A1 | 4/2012 | Kehres et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0271314 A1* | 10/2012 | Stemniski .......... A61B 17/1775 606/87 |
| 2013/0261628 A1 | 10/2013 | Burley et al. |
| 2014/0020690 A1 | 1/2014 | Triplett |
| 2014/0188236 A1 | 7/2014 | McGinley et al. |
| 2014/0243836 A1 | 8/2014 | Bake et al. |
| 2014/0270065 A1 | 9/2014 | Aram et al. |
| 2014/0275955 A1 | 9/2014 | Crawford et al. |
| 2014/0276853 A1 | 9/2014 | Long et al. |
| 2014/0277538 A1 | 9/2014 | Sander |
| 2014/0324053 A1 | 10/2014 | Stemniski et al. |
| 2015/0134071 A1 | 5/2015 | Luna et al. |
| 2015/0320567 A1 | 11/2015 | Terrill et al. |
| 2016/0022283 A1 | 1/2016 | Wallace et al. |
| 2016/0051267 A1 | 2/2016 | Sander |
| 2016/0262903 A1 | 9/2016 | West |
| 2017/0079798 A1 | 3/2017 | Forsell |
| 2017/0112509 A9 | 4/2017 | Lancianese et al. |
| 2017/0224383 A1 | 8/2017 | Wong |
| 2018/0055648 A1 | 3/2018 | Dhillon et al. |
| 2018/0303490 A1 | 10/2018 | Loring et al. |
| 2019/0070012 A1 | 3/2019 | Leemrijse et al. |
| 2019/0209080 A1 | 7/2019 | Gullotti et al. |
| 2019/0365394 A1 | 12/2019 | Abt et al. |
| 2020/0008959 A1 | 1/2020 | Oh et al. |
| 2020/0015867 A1 | 1/2020 | Luna et al. |
| 2020/0113712 A1 | 4/2020 | Luna et al. |
| 2020/0330238 A1 | 10/2020 | Calamel et al. |
| 2020/0337850 A1 | 10/2020 | Reiley |
| 2021/0378753 A1 | 12/2021 | Christen et al. |
| 2022/0022894 A1 | 1/2022 | Allard et al. |
| 2022/0280307 A1 | 9/2022 | Haddad et al. |
| 2022/0316504 A1 | 10/2022 | Kubacki |

FOREIGN PATENT DOCUMENTS

| | | |
|---|---|---|
| CN | 101111197 | 1/2008 |
| DE | 2306552 | 8/1974 |
| DE | 3516743 | 11/1986 |
| DE | 44 34 539 | 4/1996 |
| DE | 19501069 | 7/1996 |
| DE | 10123517 C1 | 11/2002 |
| DE | 20303498 | 8/2003 |
| DE | 202008017199 | 3/2009 |
| DE | 202008017200 | 3/2009 |
| EP | 0377901 | 10/1989 |
| EP | 0385930 | 9/1990 |
| EP | 0528080 | 2/1993 |
| EP | 0530804 | 10/1993 |
| EP | 0626156 | 11/1994 |
| EP | 0512529 | 7/1995 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 2124832 | 12/2009 |
| EP | 2742877 | 8/2014 |
| EP | 3878383 | 9/2021 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2000093435 | 4/2000 |
| JP | 2002-102236 | 4/2002 |
| JP | 2007521042 A | 8/2007 |
| JP | 2008-537689 | 9/2008 |
| JP | 2009515610 | 4/2009 |
| JP | 2012527285 A | 11/2012 |
| JP | 2016512136 A | 4/2016 |
| JP | 2016531614 A | 10/2016 |
| JP | 2018149333 A | 9/2018 |
| WO | WO 87/02882 | 5/1987 |
| WO | WO 90/009769 | 9/1990 |
| WO | 1991003982 A1 | 4/1991 |
| WO | WO 93/004710 | 3/1993 |
| WO | WO 93/009819 | 5/1993 |
| WO | WO 93/025157 | 12/1993 |
| WO | WO 95/027450 | 10/1995 |
| WO | WO 95/028688 | 10/1995 |
| WO | WO 95/030390 | 11/1995 |
| WO | WO 95/032623 | 12/1995 |
| WO | WO 96/024302 | 8/1996 |
| WO | WO 97/025942 | 7/1997 |
| WO | WO 97/026847 | 7/1997 |
| WO | WO 97/027885 | 8/1997 |
| WO | WO 97/038676 | 10/1997 |
| WO | WO 98/012994 | 4/1998 |
| WO | WO 98/20816 | 5/1998 |
| WO | WO 98/030617 | 7/1998 |
| WO | WO 98/32384 | 7/1998 |
| WO | WO 99/002654 | 1/1999 |
| WO | WO 99/008598 | 2/1999 |
| WO | WO 99/008728 | 2/1999 |
| WO | WO 99/042061 | 8/1999 |
| WO | WO 99/047186 | 9/1999 |
| WO | WO 99/051719 | 10/1999 |
| WO | WO 99/056674 | 11/1999 |
| WO | WO 00/009179 | 2/2000 |
| WO | WO 00/015153 | 3/2000 |
| WO | WO 00/035346 | 6/2000 |
| WO | WO 00/048550 | 8/2000 |
| WO | WO 00/059411 | 10/2000 |
| WO | WO 00/074554 | 12/2000 |
| WO | WO 01/010356 | 2/2001 |
| WO | WO 01/017463 | 3/2001 |
| WO | WO 01/019254 | 3/2001 |
| WO | WO 01/035968 | 5/2001 |
| WO | WO 01/045764 | 6/2001 |
| WO | WO 01/068800 | 9/2001 |
| WO | WO 01/070142 | 9/2001 |
| WO | WO 01/091672 | 12/2001 |
| WO | WO 02/000270 | 1/2002 |

(56) References Cited

FOREIGN PATENT DOCUMENTS

| | | |
|---|---|---|
| WO | WO 02/000275 | 1/2002 |
| WO | WO 02/002158 | 1/2002 |
| WO | WO 02/022013 | 3/2002 |
| WO | WO 02/022014 | 3/2002 |
| WO | WO 02/023483 | 3/2002 |
| WO | WO 02/034310 | 5/2002 |
| WO | WO 02/036147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2003/065907 | 8/2003 |
| WO | WO 04/043305 | 5/2004 |
| WO | WO 04/049981 | 6/2004 |
| WO | 2005041823 A1 | 5/2005 |
| WO | WO 05/051239 | 6/2005 |
| WO | WO 05/051240 | 6/2005 |
| WO | WO 06/060795 | 6/2006 |
| WO | WO 06/127283 | 11/2006 |
| WO | WO 07/041375 | 4/2007 |
| WO | WO 2007/061983 | 5/2007 |
| WO | WO 07/092841 | 8/2007 |
| WO | WO 08/112996 | 9/2008 |
| WO | WO 08/157412 | 12/2008 |
| WO | WO 2009/001083 | 12/2008 |
| WO | WO 09/111639 | 9/2009 |
| WO | WO2009143374 | 11/2009 |
| WO | WO2009158522 | 12/2009 |
| WO | WO 2010/099142 | 9/2010 |
| WO | WO 2010/120346 | 10/2010 |
| WO | WO 2010/121147 | 10/2010 |
| WO | WO2010135156 | 11/2010 |
| WO | WO 2011/110374 | 9/2011 |
| WO | WO2012121726 | 9/2012 |
| WO | 2012151589 A1 | 11/2012 |
| WO | WO2014020561 | 2/2014 |
| WO | 2016028270 A1 | 2/2016 |
| WO | 2019009891 A1 | 1/2019 |
| WO | WO2019022769 | 1/2019 |
| WO | WO2019009891 | 4/2019 |
| WO | WO2019213122 | 11/2019 |
| WO | WO 2020123295 | 6/2020 |
| WO | WO 2020124047 | 6/2020 |
| WO | WO 2020124052 | 6/2020 |
| WO | WO 2020242542 | 12/2020 |
| WO | WO 20200239909 | 12/2020 |
| WO | WO 2022015877 | 1/2022 |
| WO | WO 2022094052 | 5/2022 |

OTHER PUBLICATIONS

Second Examination Report issued in connection with the Australian Patent Application No. 202028337, Apr. 22, 2022, 4 pages.
Extended European Search Report issued in connection with corresponding European Patent Application No. 201812744.9, Dec. 9, 2022, 9 pages.
First Office Action issued in connection with corresponding Japanese Patent Application No. 2021-565834, Dec. 6, 2022, 5 pages.
Andersson, et al., "Macintosh Arthroplasty in Rheumatoid Arthritis," Acta. Orthrop. Scand., 1974, pp. 245-259, 45(2).
Anonymous: "Angle bracket (fastener)—Wikipedia", May 22, 2021, 1 page.
Anonymous: "Light Tube—Wikipedia", Mar. 4, 2021, 11 pages.
Anonymous: Newtonian Telescope—Wikipedia, May 23, 2021, 6 pages.
Argenson, et al., "Is There a Place for Patellofemoral Arthroplasty?," Clinical Orthopaedics and Related Research No. 321, 1995, pp. 162-167.
Birnbaum, et al., "Computer-Assisted Orthopedic Surgery with Individual Templates and Comparison to Conventional Operation Method," Spine, Feb. 2001, pp. 365-369, vol. 26, No. 4.
Chelule, et al., "Computer Aided Design of Personalized Jigs in Total Knee Replacement," 3rd Annual Meeting of CAOS Int'l Proc., Jun. 18-21, 2003, pp. 58-59, Spain.
Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.
DePuy Synthes, "Flexible Reamers for Intramedullary Nails" Surgical Technique, 22 pages, 2017.
De Winter, et al., "The Richards Type II Patellofemoral Arthroplasty," Acta Orthop Scand, 2001, pp. 487-490, 72(5).
Delp, et al., "A Graphics-Based Software System to Develop and Analyze Models of Musculoskeletal Structures," Comput. Biol. Med., 1995, pp. 21-34, vol. 25, No. 1.
Farrar, et al., "Computed Tomography Scan Scout Film for Measurement of Femoral Axis in Knee Arthroplasty," J. Arthroplasty, 1999, pp. 1030-1031, vol. 14, No. 8.
Final Official Action for U.S. Appl. No. 13/465,547, dated Feb. 26, 2014.
First Office Action for Japanese Patent Appln. No. 2011-552091, dated Oct. 25, 2013.
Froemel, et al., "Computer Assisted Template Based Navigation for Total Knee Replacement," Documents presented at CAOS on Jun. 17, 2001, 4 pages.
Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.
Hafez, et al., "Computer-Assisted Total Hip Arthroplasty: The Present and the Future," Future Rheumatol., 2006, pp. 121-131, vol. 1.
Kim, et al., "Measurement of Femoral Neck Anteversion in 3D. Part 1: 3D Imaging Method," Med. and Biol. Eng. and Computing, 2000, pp. 603-609, vol. 38, No. 6.
Lam, et al., "X-Ray Diagnosis: A Physician's Approach," 1998, Title page and Table of Contents pages Only, ISBN 9813083247, Springer-Verlag publishers.
Lam. et al.. "VarusNalgus Alignment of the Femoral Component in Total Knee Arthroplasty," The Knee, 2003, pp. 237-241, vol. 10.
Lu, et al., "In Vitro Degradation of Porous poly(L-lactic acid) Foams," Biomaterials, Aug. 2000, pp. 1595-1605, 21(15).
Mahaisavariya, et al., "Morphological Study of the Proximal Femur: a New Method of Geometrical Assessment Using 3-Dimensional Reverse Engineering", Medical Engineering & Physics 24 (2002) pp. 617-622.
Marler, et al., "Soft-Tissue Augmentation with Injectable Alginate and Synegeneic Fibroblasts," Plastic & Reconstructive Surgery, May 2000 pp. 2049-2058, 105(6).
PCT/US2010/025143, International Preliminary Report on Patentability and Written Opinion, Sep. 9, 2011.
Portheine, et al., "Potentials of CT-based Planning and Template-based Procedure in Hip and Knee Surgery," Orth. Prac., 2000, pp. 786-791, vol. 36, English Translation with Certification.
Radermacher, "Computer Assisted Matching of Planning and Execution in Orthopedic Surgery," Slide Presentation, Nov. 29, 1993, 22 pages.
Radermacher, "Template Based Navigation—An Efficient Technique for Hip and Knee Surgery," CAOS First Asian Meet, Mar. 27-28, 2004, pp. 45-50, India.
Radermacher, et al., "Computer-Assisted Planning and Operation in Orthopedics," Orth. Prac. 36th Year, Dec. 2000, pp. 731-737, English Translation with Certification.
Rau, et al., "Small and Neat," Medical Tech. Int'l, 1993-1994, pp. 65, 67 and 69.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Slone, et al., "Body CT: A Practical Approach," 1999, Title page and Table of Contents pages Only, ISBN 007058219, McGraw-Hill.

(56) References Cited

OTHER PUBLICATIONS

Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
Stauffer, et al., "The Macintosh Prosthesis. Prospective Clinical and Gait Evaluation," Arch. Surg., 1975, pp. 717-720, 110(6).
Stout, et al., "X-RAY Structure Determination: A Practical Guide," 1989, Title page and Table of Contents pages Only, ISBN 0471607118, John Wiley & Sons.
Stryker Trauma GmbH, "Bixcut Reamer System" Osteosynthesis, 8 sheets, 2009.
Synthes, "SynReam, The Synthes Reaming System" Surgical Technique, 22 pages, 2005.
Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.
Testi, et al., "Border Tracing Algorithm Implementation for the Femoral Geometry Reconstruction," Camp. Meth. and Programs in Biomed., 2001, pp. 175-182, vol. 65.
Vandeberg, et al., "Assessment of Knee Cartilage in Cadavers with Dual-Detector Spiral CT Arthrography and MR Imaging," Radiology, Feb. 2002, pp. 430-435, 222(2).
Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).
Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.
Yusof, et al., "Preparation and Characterization of Chitin Beads as a Wound Dressing Precursor," J. Biomedical Materials Research Part A, Oct. 2000, pp. 59-68, 54(1).
Examination Report issued in connection with corresponding Indian Patent Application No. 2004/KOLNP/2013, Nov. 27, 2018, 7 pages.
First Office Action issued in connection with corresponding Chinese Patent Application No. 201610973637.8, Nov. 28, 2018, 6 pages.
First Examination Repot issued in connection with corresponding Australian Patent Application No. 2018204063, Jul. 10, 2019, 2 pages.
Second Examination Report issued in connection with corresponding Australian Patent Application No. 2019261830, May 4, 2021, 9 pages.
First Examination Repot issued in connection with corresponding Australian Patent Application No. 201926183, Dec. 21, 2020, 4 pages.
International Search Report and Written Opinion issued in connection with International Patent Application No. PCT/US2022/070130, May 13, 2022, 17 pages.
Extended European Search Report issued in connection with European Patent Application No. 22172072, filed May 4, 2023, 25 pages.
Extended European Search Report issued in connection with European Patent Application No. 23172825.4, Dec. 1, 2023, 17 pages.
Extended European Search Report issued in connection with European Patent Application No. 23180097.0, Jan. 25, 2024, 9 pages.
Extended European Search Report issued in connection with European Patent Application No. 23185897.8, Feb. 1, 2024, 11 pages.
International Search Report and Written Opinion for PCT/US2020/015373 issued Jun. 4, 2020.

\* cited by examiner

4000a (a) RESECTING THE DISTAL END OF THE TIBIA AND PROXIMAL END OF THE TALUS FORMING A RESECTED JOINT SPACE, WHEREIN THE JOINT SPACE COMPRISES A TIBIAL RESECTION SURFACE AT THE DISTAL END OF THE TIBIA AND A TALAR RESECTION SURFACE AT THE PROXIMAL END OF THE TALUS AND IS OPEN AT THE ANTERIOR SIDE — 4010a (b) POSITIONING A POWER DRIVER EQUIPPED WITH A CUTTING TOOL BIT INTO THE RESECTED JOINT SPACE FROM THE ANTERIOR SIDE — 4020c (c) CUTTING INTO THE TALAR RESECTION SURFACE USING THE POWER DRIVER UNIT — 4030c

FIG. 12G

PREPARING A TIBIA FOR RECEIVING TIBIAL IMPLANT COMPONENT OF A REPLACEMENT ANKLE

CROSS-REFERENCE TO RELATED APPLICATIONS

This application is a National Stage Application, filed under 35 U.S.C. 371, of International Patent Application No. PCT/US2020/015373, filed on Jan. 28, 2020, which claims priority to U.S. Provisional Patent Application No. 62/853,818 filed May 29, 2019, the entireties of which are incorporated herein by reference.

FIELD OF DISCLOSURE

The present disclosure relates to an ankle replacement procedure.

BACKGROUND

An ankle joint may become severely damaged and painful due to arthritis from prior ankle surgery, bone fracture, infection, osteoarthritis, post-traumatic osteoarthritis or rheumatoid arthritis, for example. Options for treating the injured ankle have included anti-inflammatory and pain medications, braces, physical therapy, amputation, joint arthrodesis, and total ankle replacement.

Current ankle joint replacement options include preparing the distal end of the tibia by drilling through the calcaneus and the talus from the bottom of the foot to access the distal end of the tibia to ream the tibial intramedullary canal. Such approaches require an additional incision in the heel. The patient's recovery time can be extended and can delay the weight-bearing time after the surgery.

A recent improved ankle joint replacement procedure involves approaching the ankle joint space with a broach from the anterior side and preparing the intramedullary canal of the tibia manually.

SUMMARY

Disclosed is a method of preparing an intramedullary canal in a tibia for receiving a tibial implant. In some embodiments, the method comprises (a) resecting the distal end of the tibia and forming a resected joint space for the tibial implant, wherein the joint space comprises a tibial resection surface at the distal end of the tibia and is open at the anterior side; (b) positioning a power driver, equipped with a cutting tool bit, into the joint space from the anterior side, wherein the cutting tool bit is aimed toward the intramedullary canal of the tibia; and (c) cutting into the intramedullary canal using the power driver to form a tibial hole or a tibial cavity. The power driver can be used in conjunction with a guide assembly that can assist alignment of the cutting tool bit.

According to another aspect of the present disclosure, the method of preparing an intramedullary canal in a tibia for receiving a tibial implant can involve positioning the power driver, equipped with a cutting tool bit, into the joint space from the posterior side.

According to another aspect of the present disclosure, the method of preparing an intramedullary canal in a tibia for receiving a tibial implant can involve positioning the power driver, equipped with a cutting tool bit, into the joint space from the lateral side.

Also disclosed is a power driver adapter configured for cutting into an intramedullary canal of a tibia. The power driver adapter comprises an elongated body having a driving end, a cutting tool bit receiving end, and a longitudinal axis. The driving end comprises a drive shaft coaxially located with the longitudinal axis and is configured to mate with a power delivering unit that rotates the drive shaft coaxially about the longitudinal axis. The cutting tool bit receiving end comprises a cutting tool bit receiving base that is configured for engaging with a cutting tool bit and rotates the cutting tool bit for cutting action, where the cutting tool receiving base rotates with a rotational axis that is orthogonal to the longitudinal axis of the elongated body and translates superiorly and inferiorly. The elongated body comprises a series of gears connecting the drive shaft to the cutting tool bit receiving end. The series of gears are configured in an arrangement that converts the coaxial rotation of the drive shaft to the rotation and translation of the cutting tool bit receiving base.

A surgical instrument kit that includes the power driver adapter is also disclosed.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

DETAILED DESCRIPTION

Figure 1:
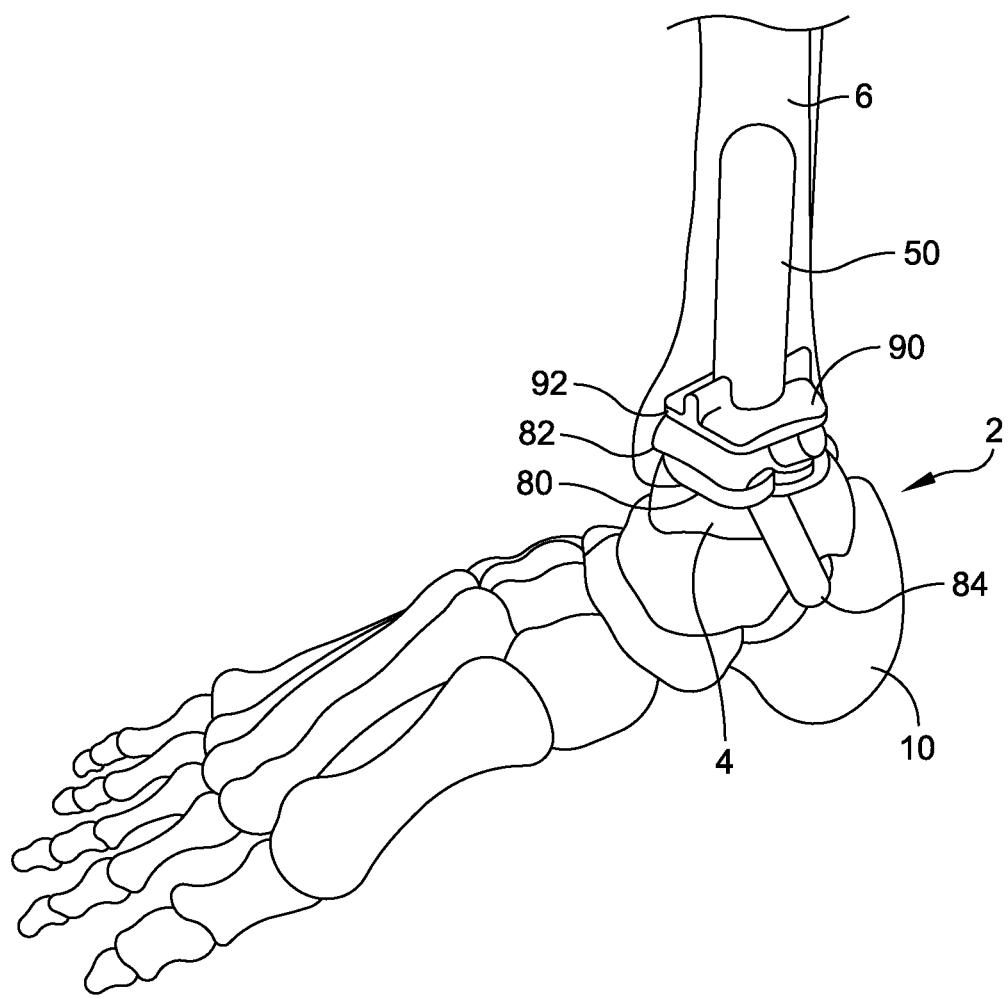
FIG. 1 is an illustration of an ankle joint.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

FIG. 1 illustrates an anatomic view of an ankle joint 2. The ankle joint 2 comprises a talus 4 in contact with a tibia 6 and a fibula (not labelled). A calcaneus 10 is located adjacent to the talus 4. In total ankle replacements, the talus 4 and the tibia 6 may be resected, or cut, to allow insertion of a talar implant and a tibial implant.

A total ankle replacement system can include a talar implant 80 and a tibial implant 90. The talar implant 80 can include an articulation surface 82 configured to mimic a natural articulation surface of the talus 4. The talar implant 80 can have a stem 84 that extends into the talus 4 to anchor the talar implant 80. A tibial implant 90 can be sized and configured for installation into the tibia 6. The tibial implant 90 can include a body comprising an articulation surface 92 configured to mimic a natural articulation of the tibia 6 and a tibial stem 50 extending into the intramedullary canal of the tibia 6 to anchor the tibial implant 90. The articulation surfaces 82, 92 of the respective implants 80, 90 replace the natural ankle joint surfaces, which are removed, to restore a range of motion that mimics the natural joint.

Figure 2:
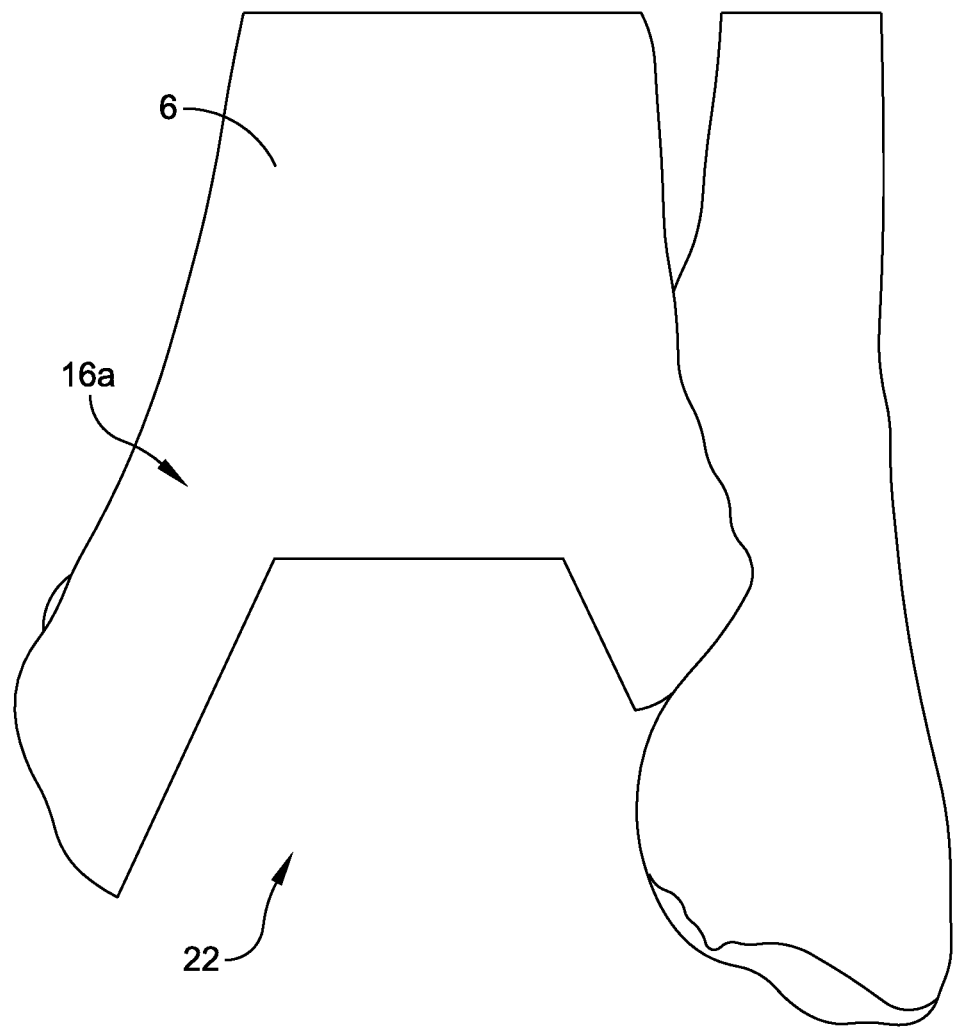
FIG. 2 is a representation of a resected joint space at the distal end of a tibia for receiving a tibial ankle replacement implant.

FIG. 2 is an illustration of a resected tibial end 16a of the tibia 6 in a human ankle showing the resected joint space 22.

Referring to FIGS. 3-5, and 9-11, a power driver 100 configured for cutting into an intramedullary canal of a tibia is disclosed. The power driver 100 comprises a power driver unit 300 for hand-held operation and a power driver adapter 200.

Preferably, the power driver unit 300 is a handheld drill-like power tool that can rotatably drive the power driver adapter 200 and comprises a chuck 310 that engages the drive shaft 222 of the power driver adapter 200.

Figure 10A:
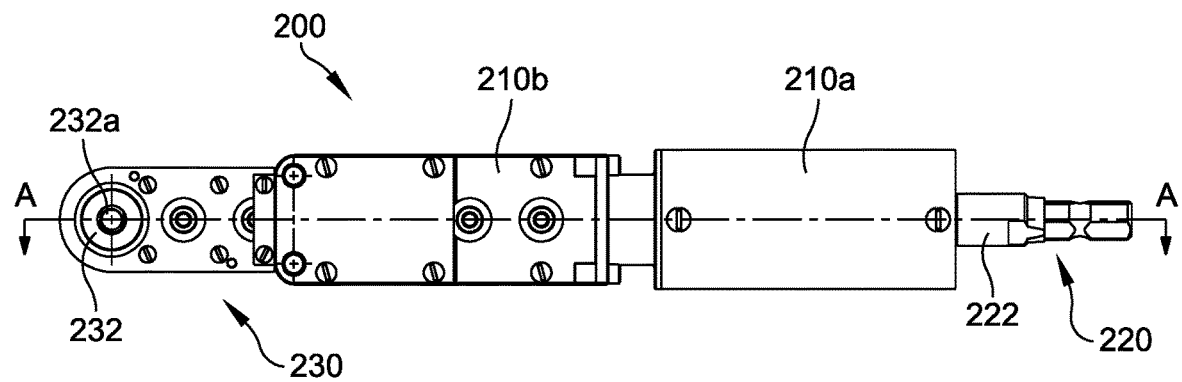
FIG. 10 is a top-down view illustration of the power driver of FIG. 9.
Figure 11A:
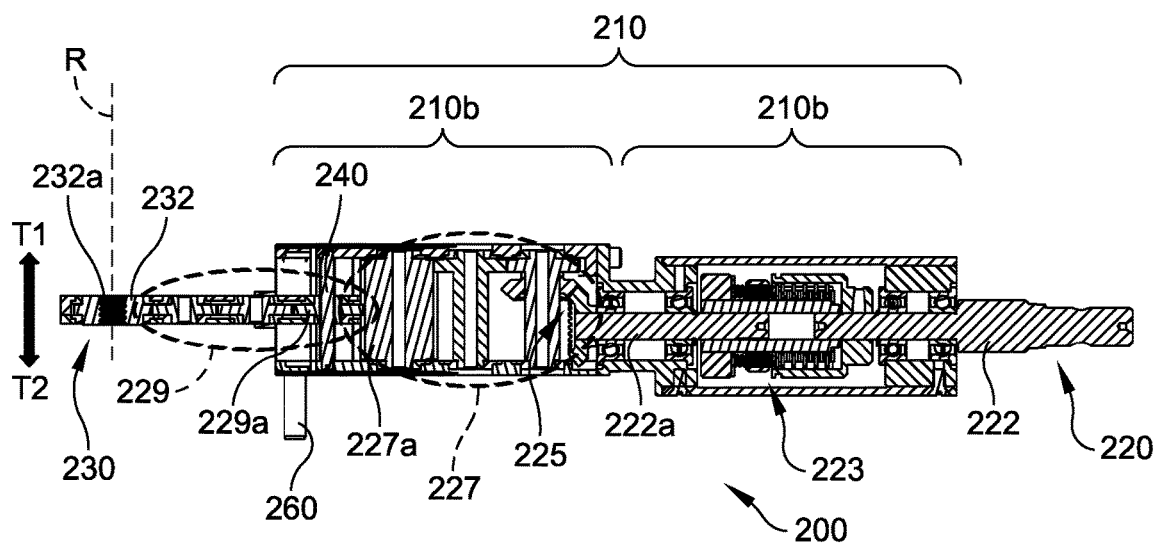
FIG. 11A is a cross-sectional view of the power driver taken through the line A-A shown in FIG. 10.
Figure 9B:
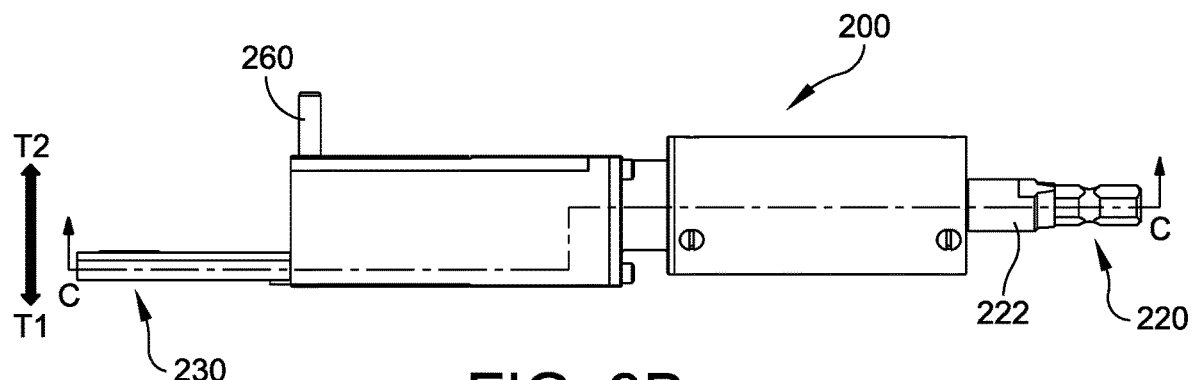
Figure 10B:
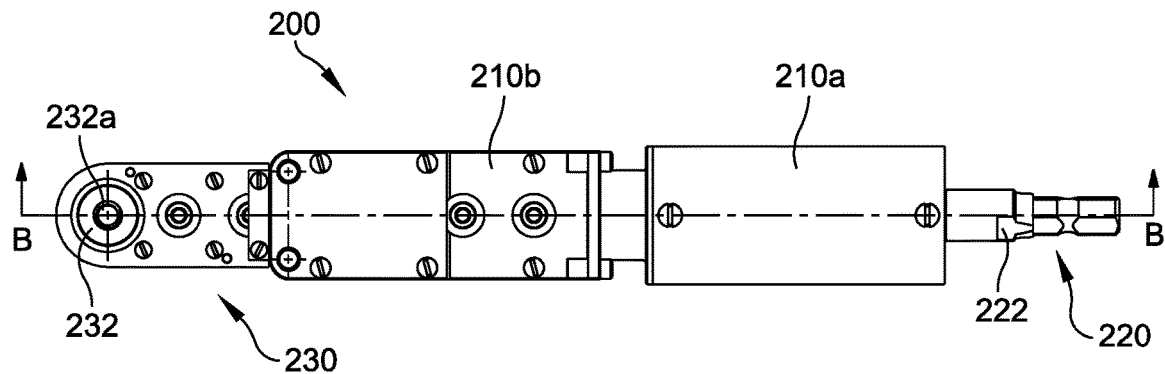
Figure 11B:
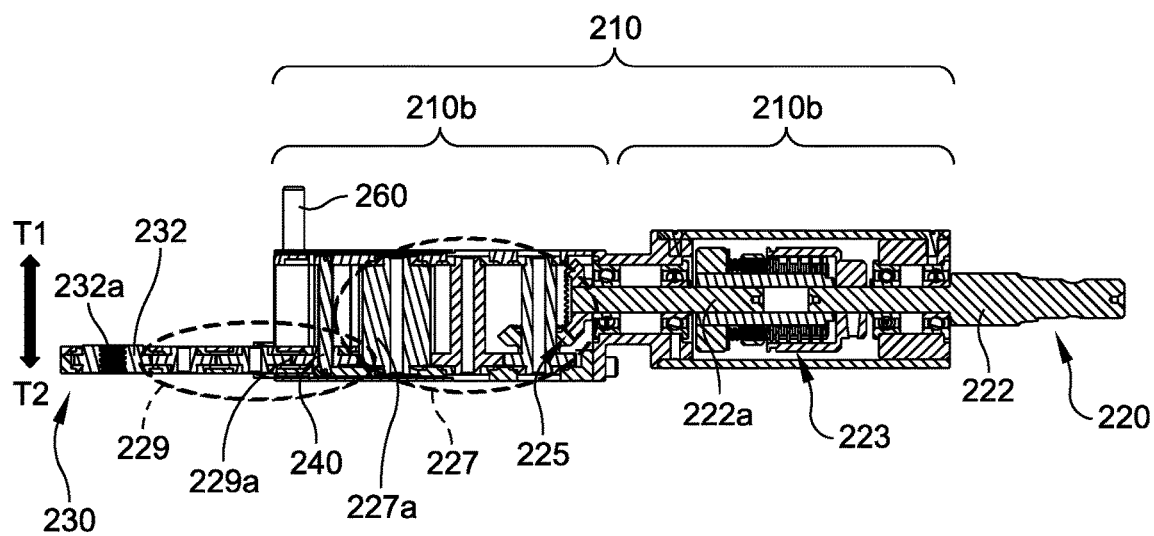
FIG. 11B is another cross-sectional view of the power driver taken through the line A-A shown in FIG. 10 in which the cutting tool bit receiving portion is in a START position.
Figure 11C:
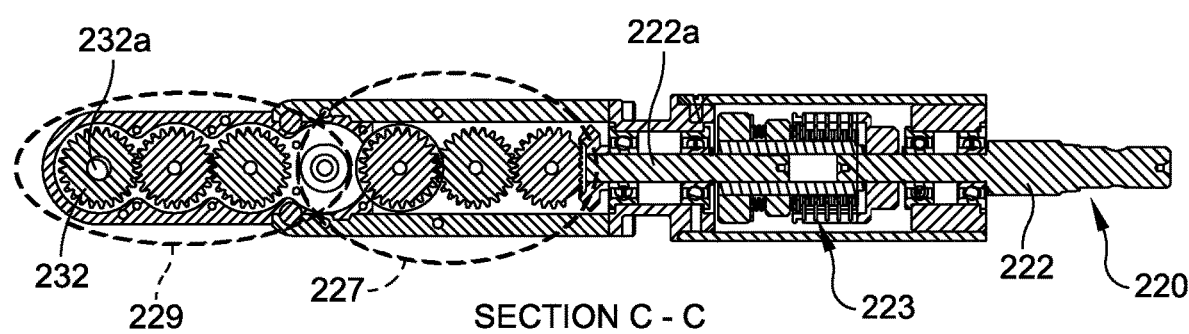
FIG. 11C is a cross-sectional view of the power driver taken through the line C-C shown in FIG. 9B.

As shown in FIGS. 3-5, and 9-11, the power driver adapter 200 comprises an elongated body 210 having a first end 220, a second portion 230, and a longitudinal axis L. The first end 220 is configured as a driving end and has a drive shaft 222 coaxially located with the longitudinal axis L and configured to engage with the power driver unit 300 that rotates the drive shaft 222 coaxially about the longitudinal axis L. The second portion 230 is configured as a cutting tool bit receiving portion. The cutting tool bit receiving portion 230 is configured to engage with a cutting tool bit 500 and rotates the cutting tool bit 500 for a cutting action. For example, as shown in FIGS. 10 and 11, the cutting tool bit receiving portion 230 can be provided with a cutting tool bit receiving base 232 that is configured to receive the cutting tool bit 500 and securely hold the bit. The cutting tool bit receiving base 232 is configured to rotate about a rotational axis R that is orthogonal to the longitudinal axis L.

The cutting tool bit receiving base 232 in the illustrated embodiment is a disc-like piece that comprises a threaded hole 232a into which the cutting tool bit 500 can thread into. The cutting tool bit 500 that is configured for attaching to the cutting tool bit receiving base 232 comprises a threaded base stem (not shown). In some other embodiments, the cutting tool bit receiving base 232 can comprise a socket hole instead for receiving the cutting tool bit 500. The socket hole can have a square hole configuration or a hexagonal hole configuration and can have a spring-loaded detent system for holding the cutting tool bit 500. These are just examples and there are other suitable configurations for engaging the cutting tool bit receiving base 232 with the cutting tool bit 500 that would be readily understood by those of ordinary skill in the art.

The elongated body 210 comprises a first portion 210a and a second portion 210b. The elongated body 210 comprises a slip clutch in the first portion 210a and a series of gears in the second portion 210b that connect the drive shaft 222 to the cutting tool bit receiving portion 230. The series of gears are configured in an arrangement that converts the coaxial rotation of the drive shaft 222 to the rotation of the cutting tool bit receiving base 232. An example of such series of gears is shown in the cross-sectional view of the elongated body 210 in FIG. 11.

The first portion 210*a* comprises a drive shaft extension piece 222*a* that is connected to the drive shaft 222 by a slip-clutch mechanism 223. When the cutting tool bit receiving portion 230 reaches the bottom (the START) or the top (FINISH) position against the housing of the second portion 210*b*, the slip clutch 223 allows the drive shaft 222 to continue to be turned by the power driver 300 while the drive shaft extension piece 222*a* (and, in turn, the spur gears 227) stop turning. The second portion 210*b* comprises a group of spur gears 227 for transferring the rotational motion to the cutting tool bit receiving base 232. Between the group of spur gears 227 and the drive shaft 222*a*, a bevel gear arrangement 225 is provided to convert the coaxial rotation motion of the drive shaft 222, 222*a*, into the orthogonally oriented rotation motion of the cutting tool bit receiving base 232.

In some embodiments, the cutting tool bit receiving base 232 is a spur gear and the cutting tool receiving portion 230 can comprise one or more additional spur gears 229 that connects the cutting tool bit receiving base 232 with the group of spur gears 227. The cutting tool bit receiving base 232 and the additional spur gears in the group of spur gears 227 have a short or low profile and have a disc-like shape, which allows the cutting tool bit receiving portion 230 to maintain a low profile for positioning the cutting tool bit receiving portion 230 into the resected joint space 22. The last spur gear 227*a* among the group of spur gears 227 engages with the first spur gear 229*a* among the additional spur gears 229.

The cutting tool bit 500 can be one of many types of cutting tool bits that may be used in orthopedic procedures. In some embodiments of the power driver adapter 200, the cutting tool bit 500 is a reamer bit.

In some embodiments of the power driver adapter 200, the cutting tool bit receiving portion 230 can be configured to translate linearly along directions that are coaxial to the rotational axis R of the cutting tool bit 500 and orthogonal to the longitudinal axis L. The directions of the linear translation motion are illustrated by the arrows T1 and T2 in FIG. 11. The illustration of FIG. 11 is a sectional view seen from the side. Therefore, when the power driver adapter 200 is in operational use in the resected joint space 22, the arrow T1 represents the anatomical superior direction and the arrow T2 represents the anatomical inferior direction.

In some embodiments, in addition to the group of spur gears 227, the second portion 210*b* further comprises a helical thread arrangement that enables the linear translation of the cutting tool bit receiving portion 230. In the exemplary structure shown in FIG. 11, this helical thread arrangement comprises a helical threaded stem 240 and the first spur gear 229*a* among the additional spur gears 229 in the cutting tool bit receiving portion 230. The first spur gear 229*a* comprises a helical threaded hole in its rotational center that engages the helical threaded stem 240, which extends through the helical threaded hole. The helical threaded stem 240 does not rotate. When the cutting tool bit 500 is being rotated for a cutting action, as the first spur gear 229*a* rotates, its helical threaded hole cooperates with the helical thread on the helical threaded stem 240 and translates along the length of the helical threaded stem 240, thus, moving the whole cutting tool bit receiving portion 230 along the length of the helical threaded stem 240.

Depending on the rotational direction; the helical threads on the first spur gear 229*a* and the helical threaded stem 240 are appropriately handed (i.e., right handed or left handed) so that the first spur gear 229*a*, and hence the cutting tool bit receiving portion 230, translates in the direction T2 indicated by the arrow in FIG. 11 when the cutting tool bit 500 is being turned or driven in the cutting direction. Conversely, when the cutting procedure is completed, the power driving unit 300 is reversed and the cutting tool bit 500 is rotated in the opposite direction, the first spur gear 229*a* and the cutting tool receiving portion 230 will translate along the helical threaded stem 240 in the opposite direction T1.

When the power driver adapter 200 is used for reaming the distal end of a tibia, for example, the power driver adapter 200 is in position such that the cutting tool bit 500 is positioned and aimed toward the intramedullary canal of the tibia, the cutting tool receiving portion 230 would be in its START position, i.e., with the cutting tool receiving portion 230 at its most inferior position. This START configuration is shown in FIG. 11B. In FIG. 11B, one can tell that the cutting tool receiving portion 230 is in the START position because it is on the opposite side of the alignment pins 260. The function of the alignment pins 260 are described below in conjunction with FIGS. 3-5. When the power driver unit 300 is turned on to its cutting mode, as the cutting tool bit 500 turns in the cutting direction, the cutting tool holding portion 230 translates in the direction T2. This enables the cutting tool bit 500 to be driven into the intramedullary canal of the tibia without moving the whole power driver unit 300 and the power driver adapter 200. While the power driver unit 300 and the power driver adapter 200 assembly are being held stationary, the cutting tool bit 500 will automatically be driven into the intramedullary canal by the translation motion of the cutting tool bit receiving portion 230.

Figure 3:
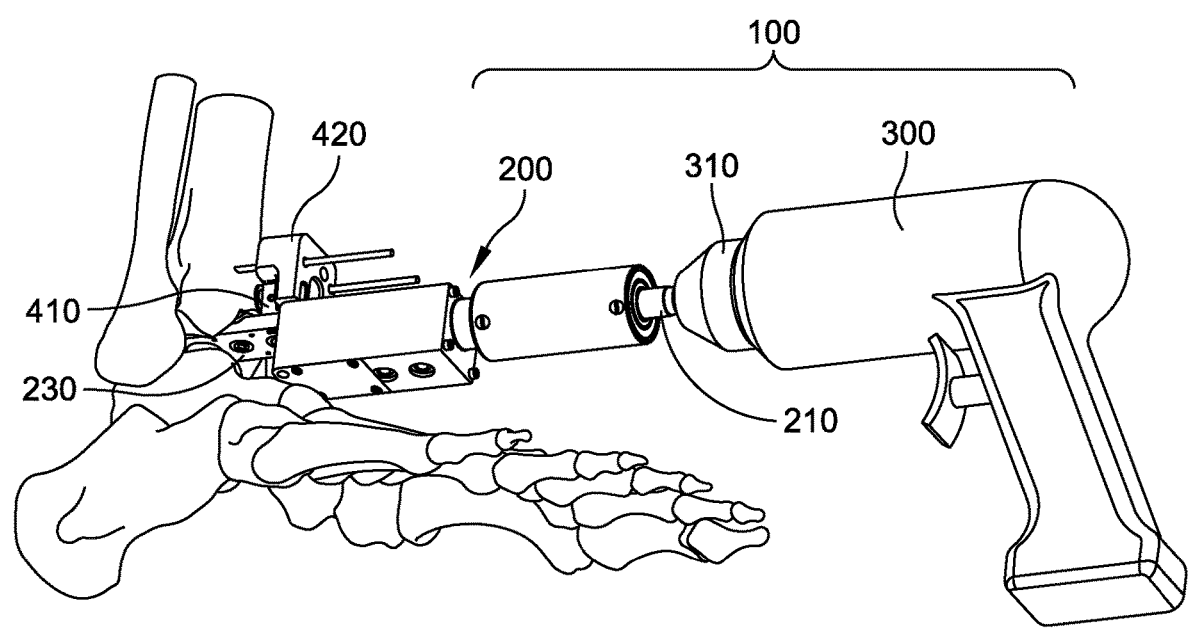
FIG. 3 is an illustration of the inventive power driver assembly of the present disclosure engaging the resected joint space of a tibia from the anterior side at the completion of the tibial preparation procedure.
Figure 4:
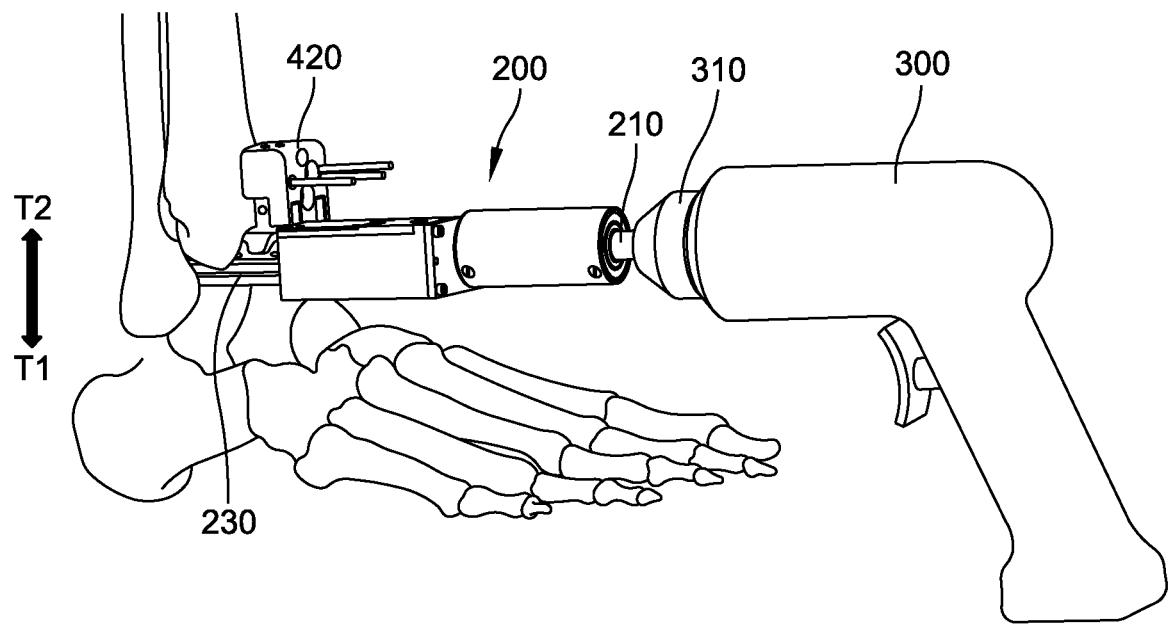
FIG. 4 is another illustration of the inventive power driver assembly of FIG. 3 seen from a different angle.
Figure 6:
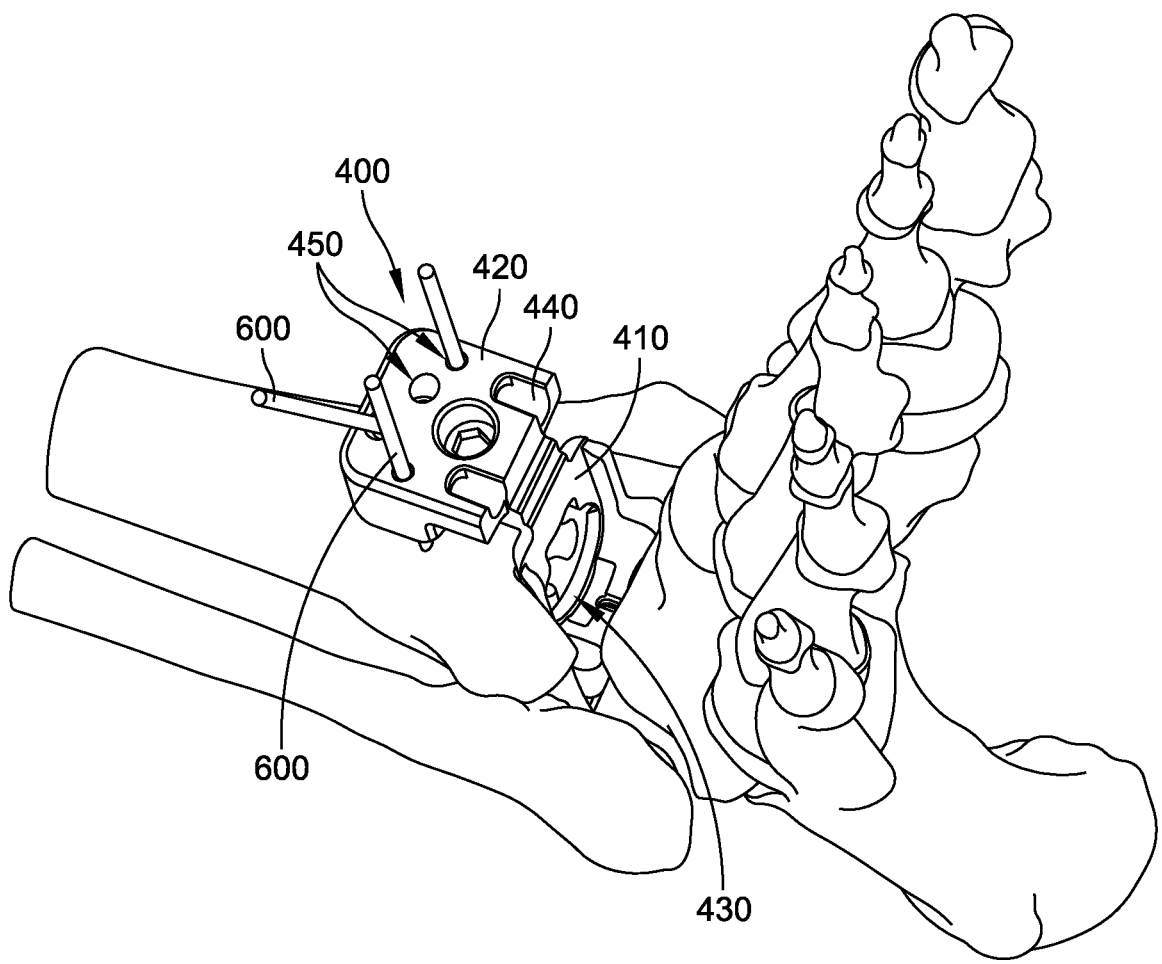
FIG. 6 is an illustration of the guide assembly installed in the resected joint space.

Referring to FIGS. 3, 4, and 6, in some embodiments, the power driver adapter 200 can be used in conjunction with a guide assembly 400 that can assist with positioning and alignment of the power driver adapter 200 in the resected joint space 22 during the procedure of preparing the intramedullary canal of the tibia. The guide assembly 400 comprises a guide portion 410 configured for attaching to the resected surface at a distal end of the tibia, wherein the guide portion comprises a hole 430 for receiving and allowing the cutting tool bit 500 to extend therethrough. The guide assembly 400 also includes a guide head portion 420 extending in the proximal direction from the guide portion 410 and configured for attaching to the anterior side of the tibia as shown in FIG. 6.

The power driver adapter 200 and the guide head portion 420 are configured to properly align and position the cutting tool bit 500 held in the power driver adapter 200 for cutting into the intramedullary canal of the tibia. The power driver adapter 200 can comprise of one or more alignment pins and the guide head portion 420 can comprise of one or more corresponding alignment slots for receiving the alignment pins to align the position of the power driver adapter 200.

Figure 5:
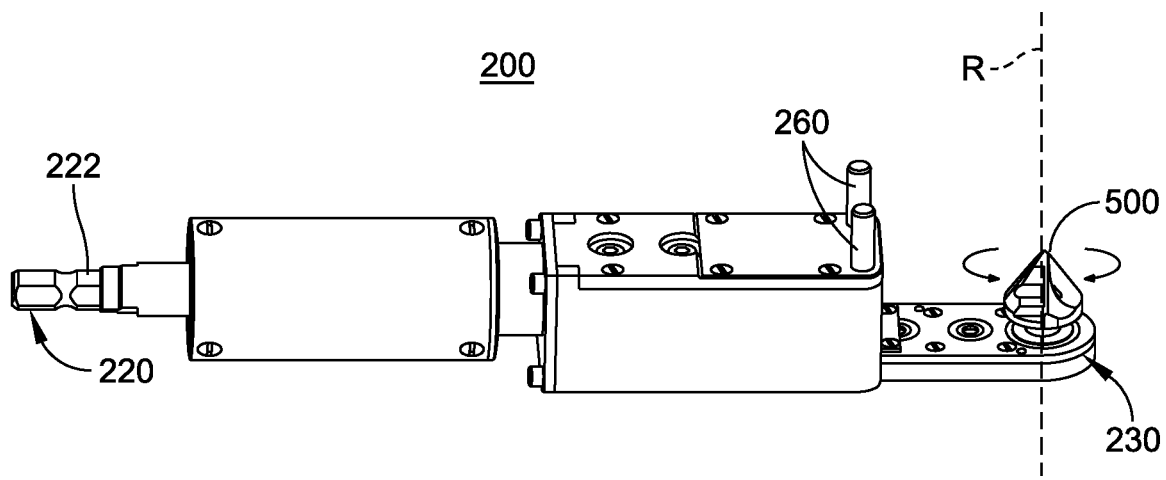
FIG. 5 is an illustration of the power driver adapter according to the present disclosure.

In the exemplary embodiment illustrated in FIGS. 4-6, the power driver adapter 200 comprises two alignment pins 260 and the guide head portion 420 comprises corresponding two alignment slots 440 for receiving the alignment pins 260. After inserting the cutting tool bit receiving portion 230 of the power driver adapter 200 into the joint space 22 from the anterior side, the two alignment pins 260 are inserted into the corresponding alignment slots 440 on the guide head portion 420. The power driver adapter 200 is oriented so that the cutting tool bit 500 is held in the cutting tool bit receiving portion 230 and positioned at the distal end of the resected tibia aimed toward the intramedullary canal of the tibia and ready to cut into the intramedullary canal of the tibia. In some embodiments, the alignment slots 440 are shaped and sized so that the alignment pins 260 and the alignment slots 440 establish a slip-fit engagement, which can help hold the power driver adapter 200 assembly securely in position during the cutting procedure. This arrangement would look very much like the ones illustrated in FIGS. 3 and 4 except for the fact that FIGS. 3 and 4 actually shows the arrangement at the end of the tibial intramedullary canal preparation procedure.

In use, after the guide assembly 400 is positioned in the resected joint space 22 as shown in FIG. 6, the guide assembly 400 can be secured to the tibia by employing one or more fixation pins, such as k-wires or Steinmann pins. The guide head portion 420 can be provided with one or more holes extending therethrough for receiving such fixation pins. In the example shown in FIG. 6, the guide head portion 420 is provided with a plurality of holes 450; fixation pins 600 are shown inserted therethrough securing the guide assembly 400 to the tibia 6.

In some embodiments, the power driver adapter 200 can be aligned within the joint space 22 without the use of the alignment guide 400. For example, the power driver adapter 200 can be configured with an alignment arms 290 like the ones shown in FIGS. 13A-13C where the alignment arms 290 and the alignment pins 292 are radiopaque. The power driver adapter 200 can be inserted into the joint space 22 and viewed under a fluoroscopy to align the cutting tool bit 500. In some embodiments, the power driver adapter 200 can be made of radiolucent material and provided with radiopaque markers (a bullseye, for example) for alignment cues.

According to another aspect of the present disclosure, a surgical instrument kit is disclosed. The surgical instrument kit comprises a power driver adapter 200 configured for cutting into an intramedullary canal of a tibia, and one or more bone cutting tool bits (e.g. one or more reaming bits 500). The structure of the power driver adapter 200 is as described above. In some embodiments, the surgical instrument kit can also comprise a guide assembly 400 whose structure is as described above.

Figure 12A:
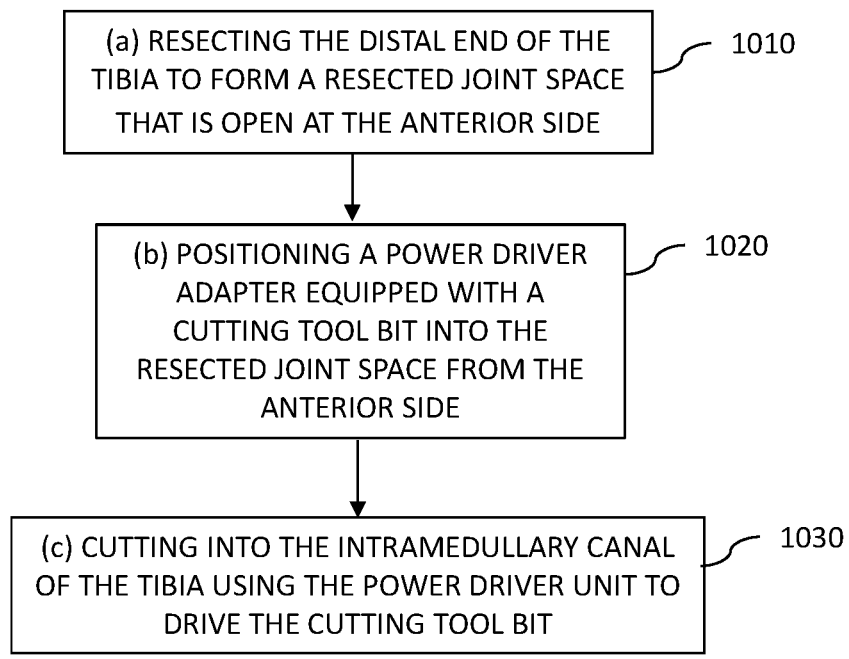
FIGS. 12A-12I are flowcharts illustrating the various embodiments of the methods for preparing the intramedullary canal of a tibia according to the present disclosure.
Figure 13A:
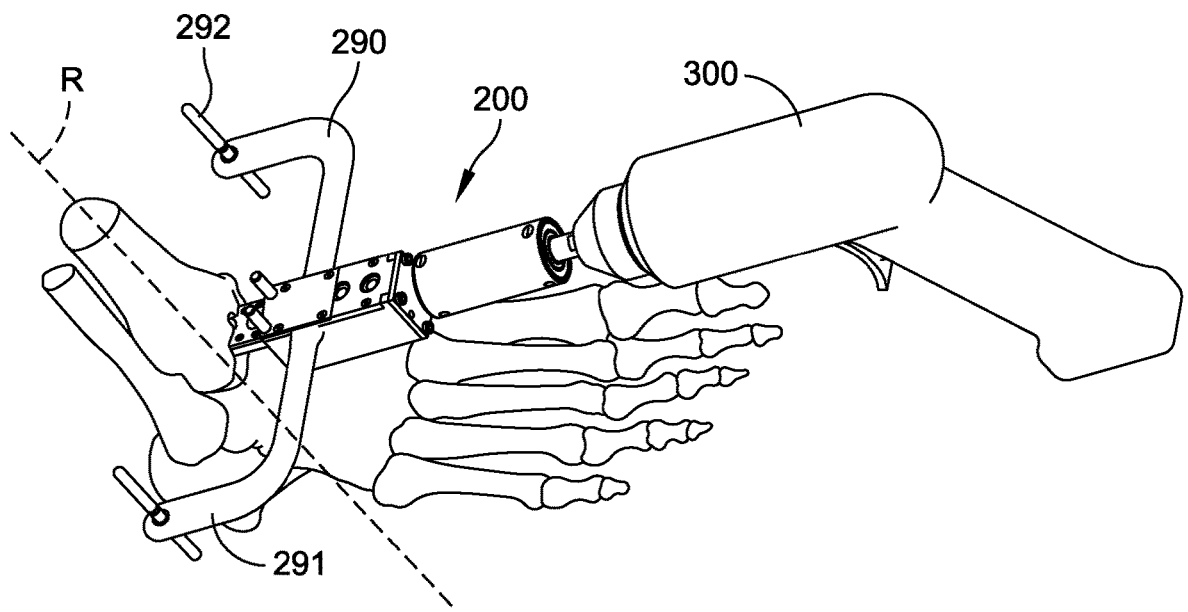
FIG. 13A-13C show an embodiment of the power driver adapter of the present disclosure having alignment arms for use in the environment.
Figure 13B:
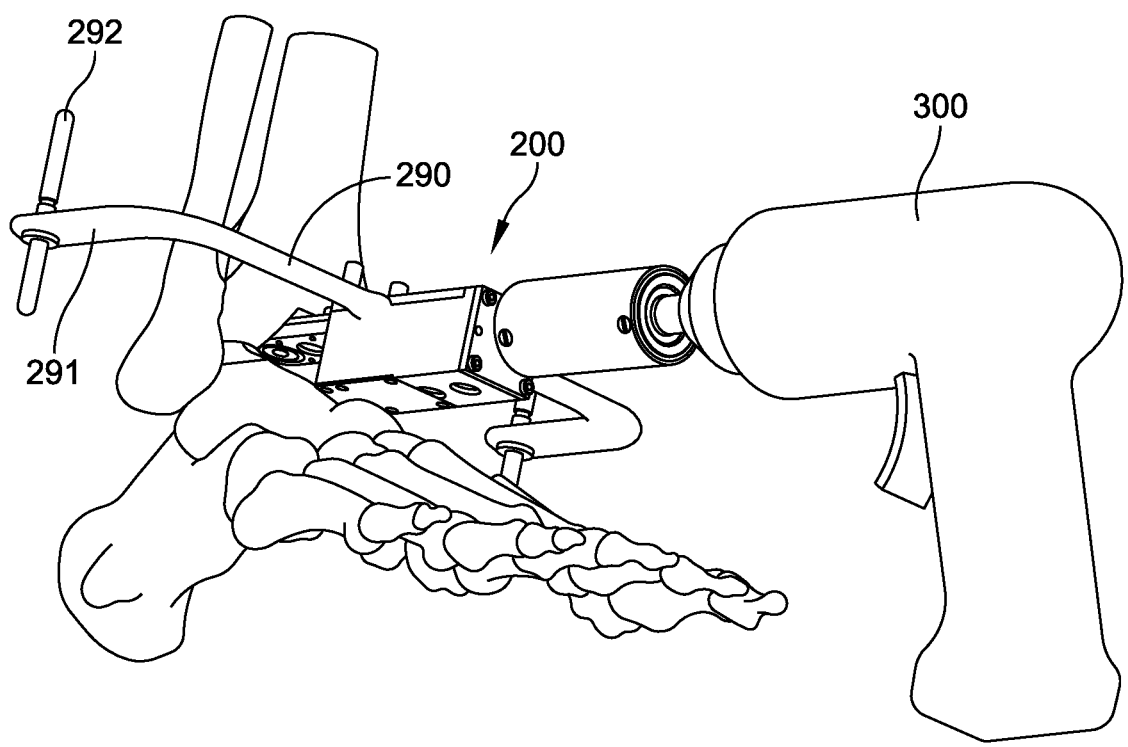
Figure 13C:
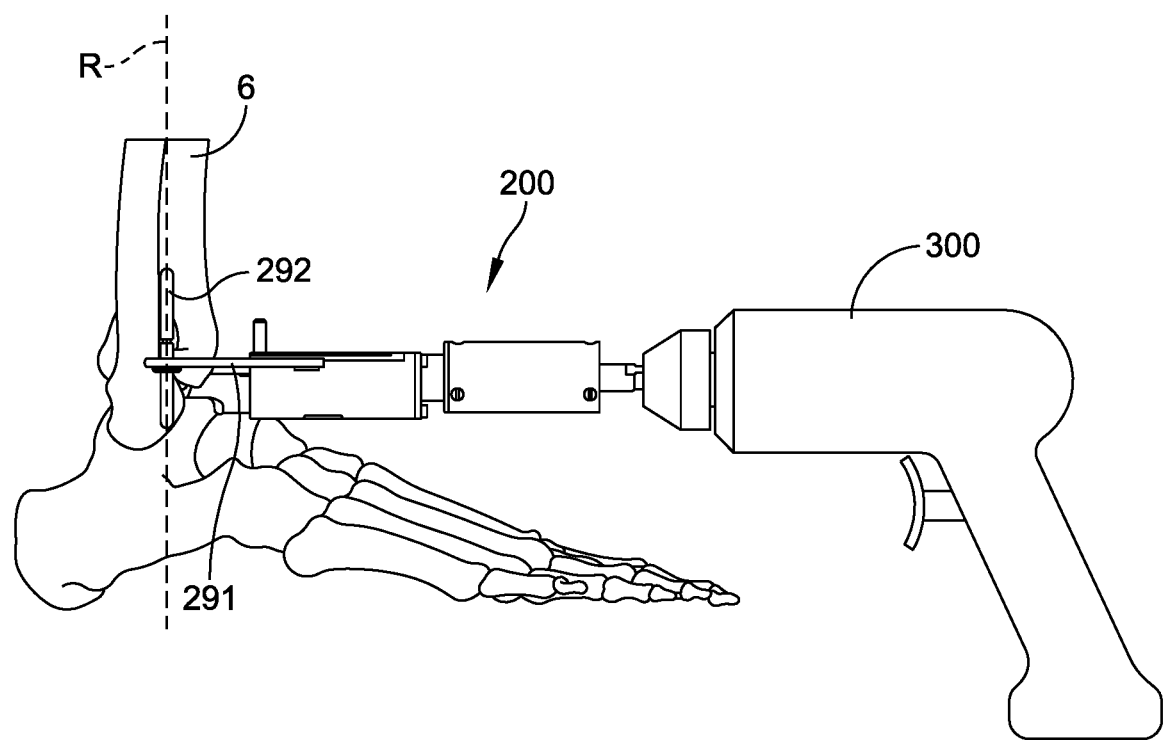

According to another aspect of the present disclosure, some methods for preparing the intramedullary canal in a tibia for receiving a tibial implant are disclosed. According to some embodiments, the flowchart 1000a in FIG. 12A in conjunction with FIGS. 13A-13C illustrates an example of such a method where the power driver adapter 200 equipped with a cutting tool bit 500 approaches the resected joint space 22 of an ankle from the anterior side for preparing the intramedullary canal in the distal end of the tibia for receiving a tibial implant according to an embodiment. The method comprises resecting the distal end of the tibia and forming a resected joint space 22 for receiving the tibial implant, where the joint space comprises a tibial resection surface at the distal end of the tibia and is open at the anterior side, see step 1010. If necessary, the proximal end of the talus may also need to be resected to properly form the resected joint space 22. Then, a power driver unit 300 with a power driver adapter 200 equipped with a cutting tool bit 500 is positioned into the joint space 22 from the anterior side, where the cutting tool bit 500 is aimed toward the intramedullary canal of the tibia, see step 1020. Next, the power driver unit 300 is turned on to drive the cutting tool bit 500 to cut into the intramedullary canal, see step 1030.

In some embodiments of the method, cutting into the intramedullary canal forms a void or a tibial cavity extending into the intramedullary canal for receiving a tibial stem or a tibial extension of an ankle replacement implant.

In the arrangement shown in FIGS. 13A-13C, an embodiment of the power driver adapter 200 that is provided with a pair of alignment arms 290 is shown. The alignment arms 290 assist with aligning the trajectory of the cutting tool bit 500 as the power driver adapter 200 is positioned into the resected joint space 22. The alignment arms 290 extend out from the power driver adapter 200 and have end portions 291 that curve around forward. The alignment arms 290 comprise of alignment posts 292 provided on the end portions 291 that represents the cutting trajectory of the cutting tool bit 500 and can be used to position the power driver adapter 200 visually while maintaining the alignment/trajectory of the cutting tool bit 500 before and during the cutting procedure. As shown in FIGS. 13A and 13C, the alignment arms 290 and the alignment posts 292 are configured so that the alignment posts 292 are parallel with the rotation axis R of the cutting tool bit 500 installed on the cutting tool bit receiving base 232 and the two alignment posts 292 are also in the same plane as the rotation axis R. This configuration allows the surgeon to use the alignment posts 292 as visual guides to align the power driver adapter 200 into the joint space 22. The side view in FIG. 13C shows the power driver adapter 200 in aligned position where the cutting tool bit's rotation axis R has been aligned with the intramedullary canal of the tibia 6 by using the alignment posts 292 as guides.

Figure 12B:
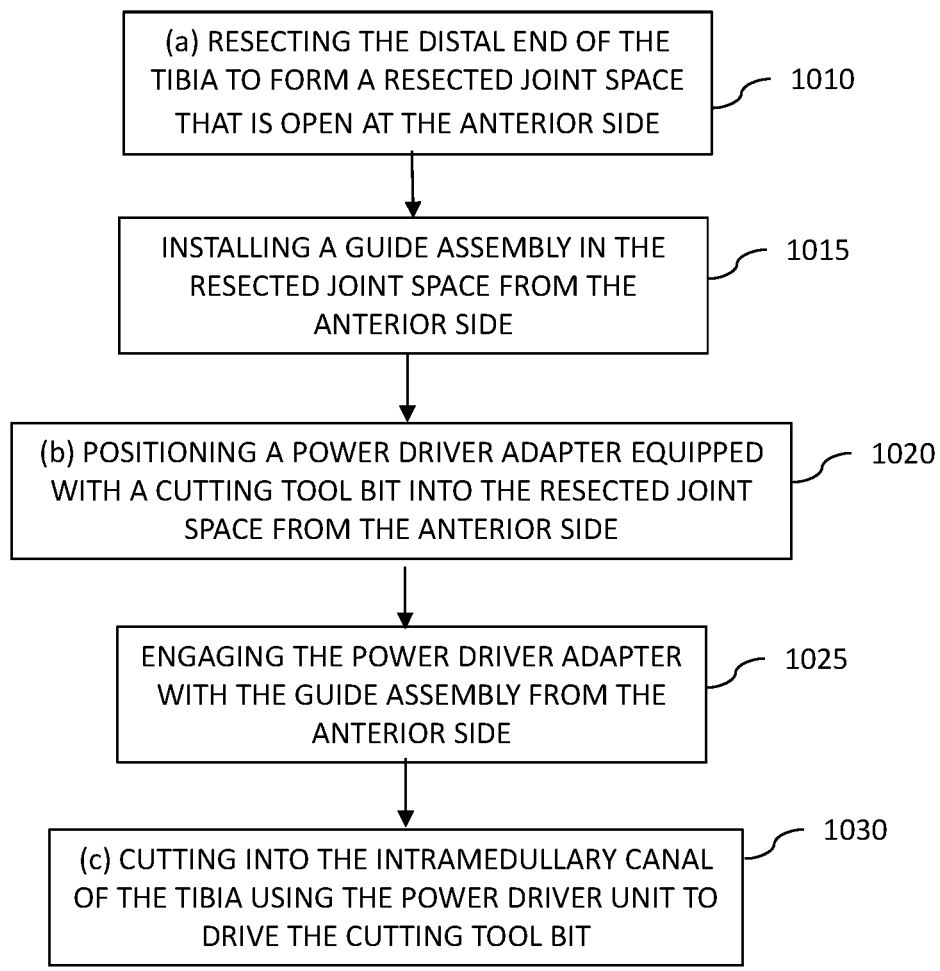

The flowchart 1000b in FIG. 12B in conjunction with FIGS. 3 and 4 illustrates another embodiment of the method in which a guide assembly 400 is used to align the trajectory of the cutting tool bit 500. The method illustrated in flowchart 1000b further comprises the step 1015 of installing a guide assembly 400 in the joint space from the anterior side of the ankle after the step 1010. Then, after positioning the power driver adapter 200 equipped with a cutting tool bit 500 into the resected joint space 22 from the anterior side in step 1020, one engages the power driver adapter 200 with the guide assembly 400 from the anterior side to align the position of the cutting tool bit 500, see step 1025. Next, the power driver unit 300 is turned on to drive the cutting tool bit 500 to cut into the intramedullary canal to prepare the intramedullary canal for a tibial implant, see step 1030.

Figure 7:
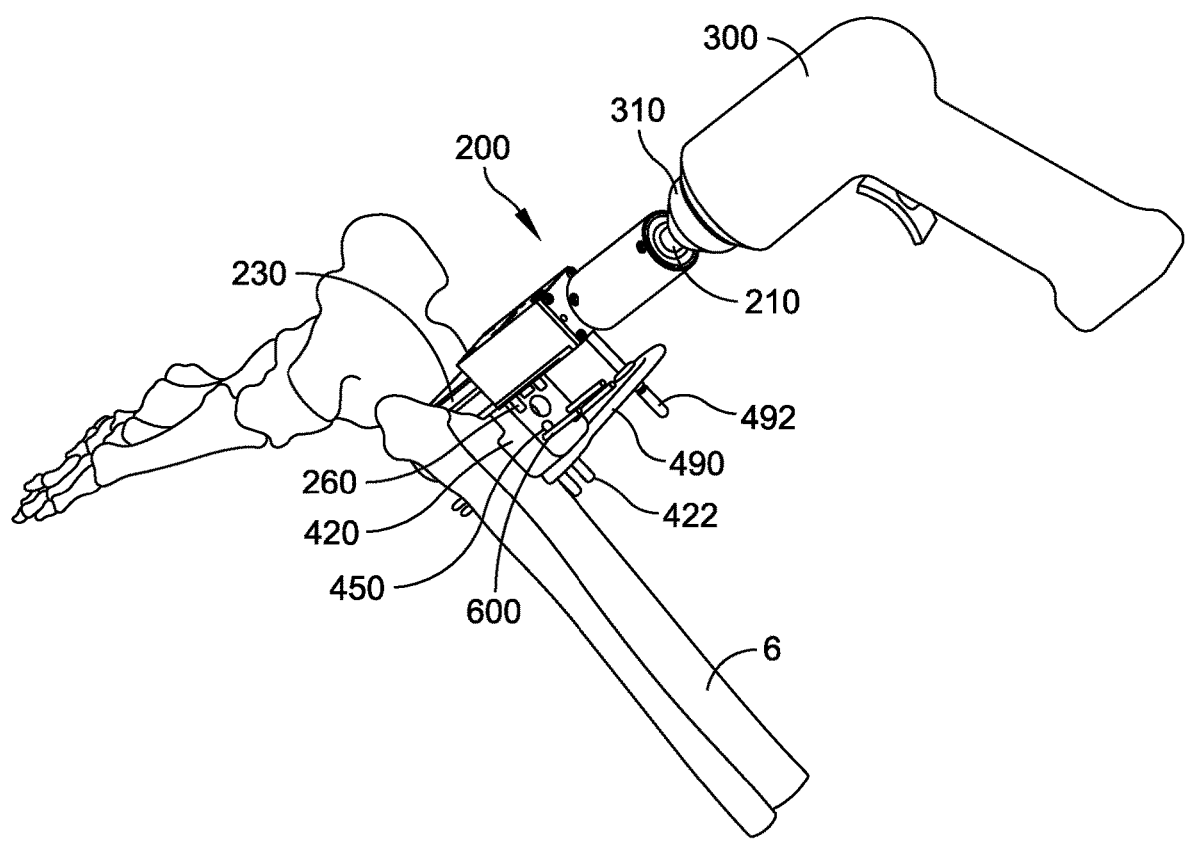
FIG. 7 is an illustration of the inventive power driver assembly of the present disclosure being positioned in the resected joint space of a tibia from the posterior side.
Figure 12C:
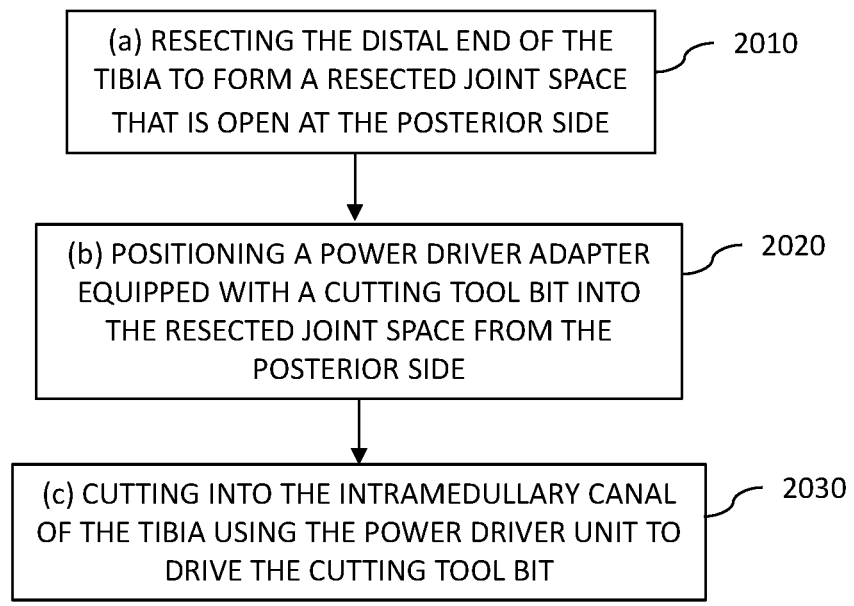

The flowchart 2000a in FIG. 12C in conjunction with FIG. 7 illustrates an example of a posterior approach method of preparing an intramedullary canal in a tibia for receiving a tibial implant according to an embodiment. The method comprises resecting the distal end of the tibia forming a resected joint space 22 for receiving the tibial implant, where the joint space comprises a tibial resection surface at the distal end of the tibia and is open at the posterior side, see step 2010. If necessary, the proximal end of the talus may also need to be resected to properly form the resected joint space 22. Then, a power driver adapter 200 equipped with a cutting tool bit 500 is positioned into the joint space 22 from the posterior side, where the cutting tool bit 500 is aimed toward the intramedullary canal of the tibia, see step 2020. Next, the power driver unit 300 is turned on to drive the cutting tool bit 500 to cut into the intramedullary canal to prepare the intramedullary canal for a tibial implant, see step 2030.

Figure 12D:
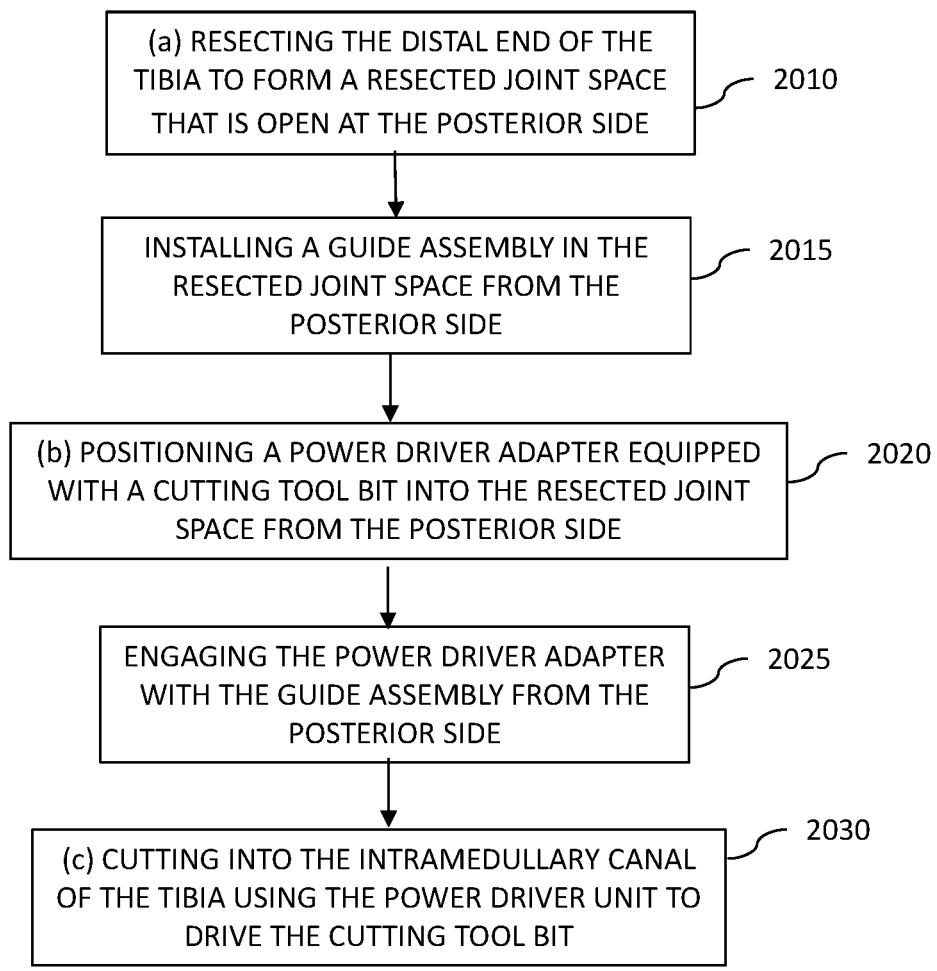

The flowchart 2000b in FIG. 12D illustrates another embodiment of the posterior approach method in which the method further comprises the step 2015 of installing a guide assembly 400 in the joint space from the posterior side of the ankle after the step 2010. Then, after positioning the power driver adapter 200 equipped with the cutting tool bit 500 into the resected joint space 22 from the posterior side in step 2020, one engages the power driver adapter 200 with the guide assembly 400 from the posterior side to align the position of the cutting tool bit 500, see step 2025. Next, the power driver unit 300 is turned on to drive the cutting tool bit 500 to cut into the intramedullary canal to prepare the intramedullary canal for a tibial implant, see step 2030.

FIG. 7 is an illustration of the posterior approach arrangement after the guide assembly 400 is positioned in the resected joint space 22. The guide head portion 420 is provided with a plurality of holes 450 for receiving one or more fixation pins 600 for securing the guide assembly 400 to the tibia 6 from the posterior side. The fixation pins 600 are shown inserted through the holes 450 securing the guide assembly 400 to the tibia 6. In this embodiment, the guide assembly 400 itself can include an alignment guide arm 490. The alignment guide arm 490 can be attached to the guide head portion 420 via an appropriate attachment mechanism. In the illustrated example, the guide head portion 420 is configured with one or more pins/screws 422 to which the alignment guide arm 490 is attached. The key feature of the alignment guide arm 490 is that it extends out sideways from the guide head portion 420 and is provided with an alignment post 492. This allows the operator/surgeon to visually align the guide assembly 400 during installation on to the tibia 6, which ensures that the cutting tool bit 500 will be properly aligned. The power driver adapter 200 equipped with the cutting tool bit 500 is then positioned into the joint space 22 from the posterior side of the patient and mated with the guide assembly 400. The alignment post 492 and the guide head portion 420 are configured so that when the power driver adapter 200 is engaged and aligned with the guide head portion 420 by slip-fitting the alignment pins 260 into the corresponding alignment slots 440 in the guide head portion 420, the alignment post 492 is in parallel relation to the rotational axis R of the cutting tool bit 500.

Figure 8:
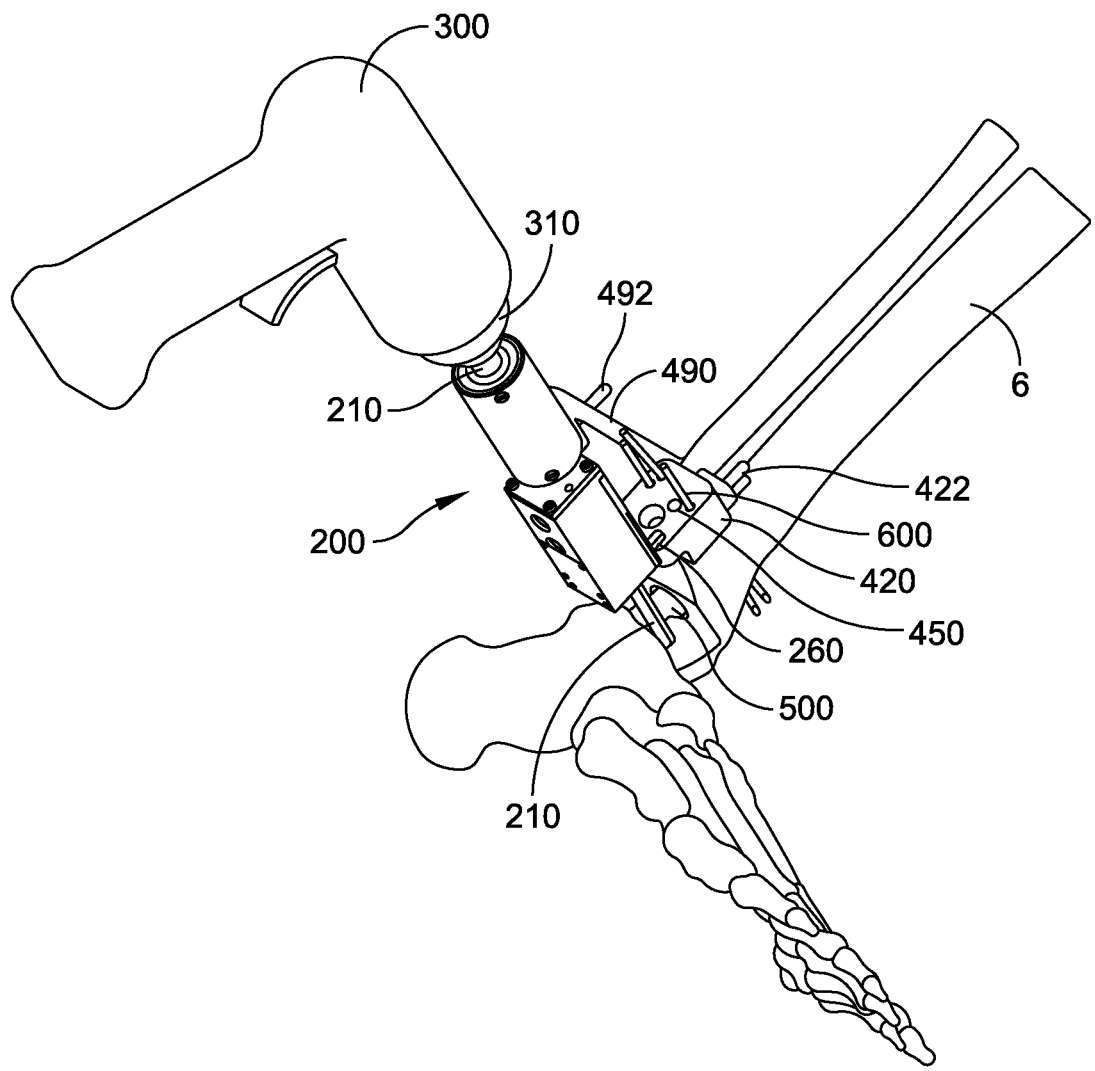
FIG. 8 is an illustration of the inventive power driver assembly of the present disclosure being positioned in the resected joint space of a tibia from the lateral side.
Figure 9A:
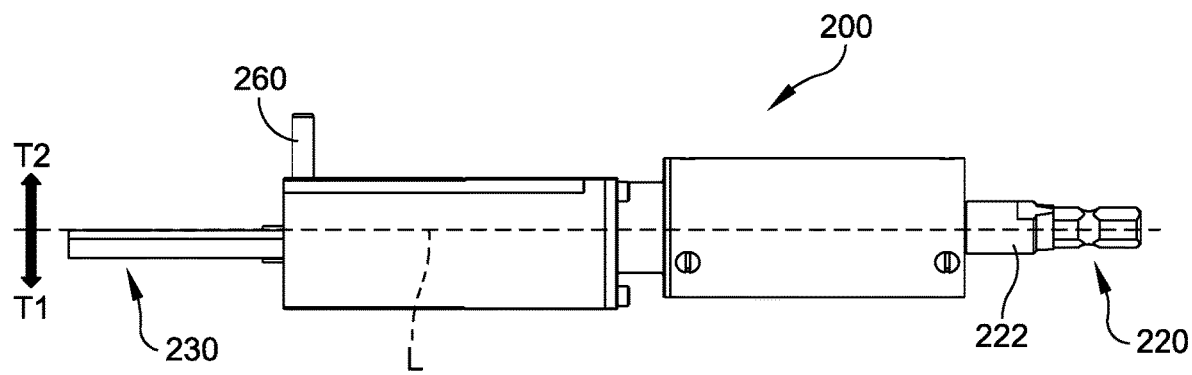
FIG. 9 is a side view illustration of the power driver of the present disclosure.
Figure 12E:
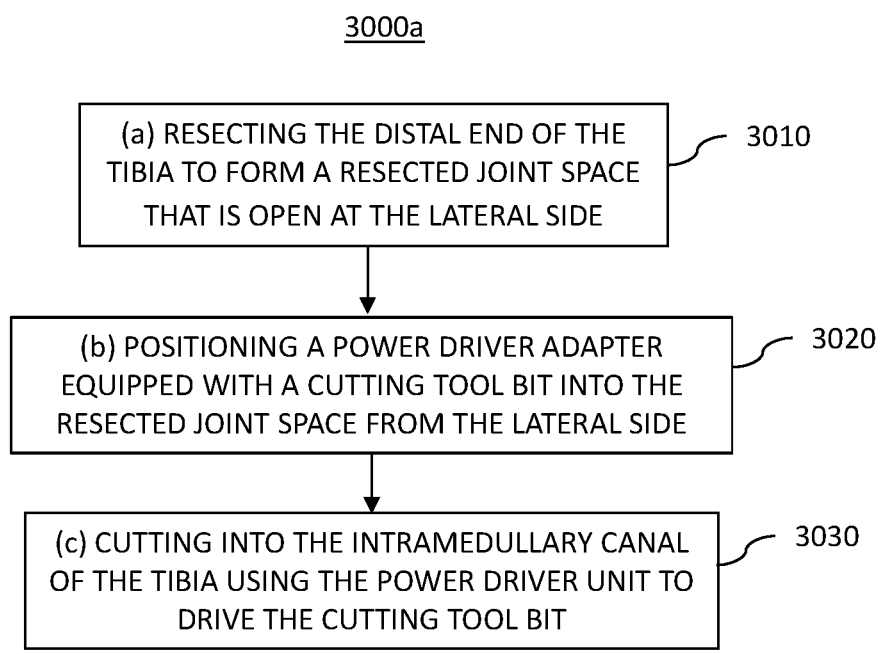

The flowchart 3000*a* in FIG. 12E in conjunction with FIG. 8 illustrates an example of a lateral approach method of preparing an intramedullary canal in a tibia for receiving a tibial implant according to an embodiment. The method comprises resecting the distal end of the tibia and, if necessary, the proximal end of the talus forming a resected joint space 22 for receiving the tibial implant, where the joint space comprises a tibial resection surface at the distal end of the tibia and is open at the lateral side, see step 3010. Then, the power driver adapter 200 equipped with the cutting tool bit 500 is positioned into the joint space 22 from the lateral side, where the cutting tool bit 500 is aimed toward the intramedullary canal of the tibia, see step 3020. Next, the power driver unit 300 is turned on to drive the cutting tool bit 500 to cut into the intramedullary canal to prepare the intramedullary canal for a tibial implant, see step 3030.

Figure 12F:
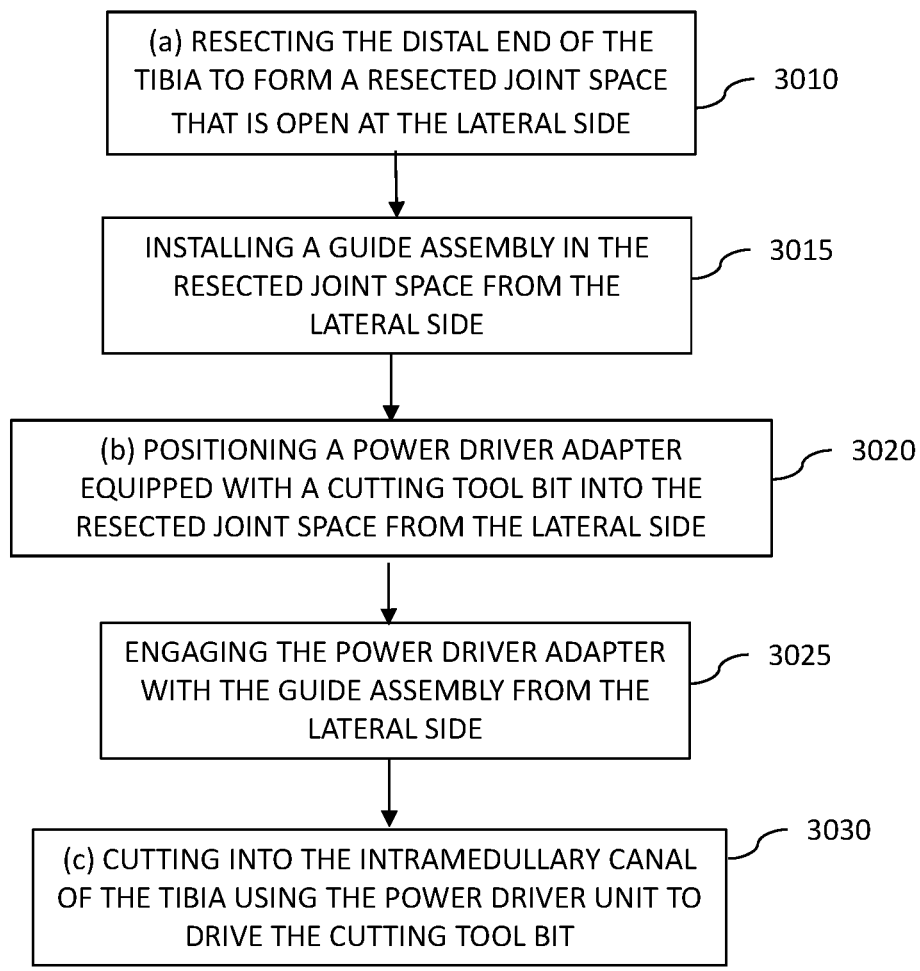

The flowchart 1000*b* in FIG. 12F illustrates another embodiment of the lateral approach method in which the method further comprises the step 3015 of installing a guide assembly 400 in the joint space from the lateral side of the ankle after the step 3010. Then, after positioning the power driver adapter 200 equipped with the cutting tool bit 500 into the resected joint space 22 from the lateral side in step 3020, one engages the power driver adapter 200 with the guide assembly 400 from the lateral side to align the position of the cutting tool bit 500, see step 3025. Next, the power driver unit 300 is turned on to drive the cutting tool bit 500 to cut into the intramedullary canal to prepare the intramedullary canal for a tibial implant, see step 3030.

FIG. 8 is an illustration of the lateral approach arrangement where the guide assembly 400 is then positioned in the resected joint space 22. The guide head portion 420 is provided with a plurality of holes 450 for receiving one or more fixation pins 600 for securing the guide assembly 400 to the tibia 6 from the posterior side. The fixation pins 600 are shown inserted through the holes 450 securing the guide assembly 400 to the tibia 6. The power driver adapter 200 equipped with the cutting tool bit 500 is then positioned into the joint space 22 from the lateral side of the patient and mated with the guide assembly 400. Similar to the description provided above in connection with FIG. 7, in some embodiments of the lateral approach arrangement, the guide assembly 400 can include an alignment guide arm 490 that is provided with an alignment post 492. The function of the alignment guide arm 490 and the alignment post 492 in this embodiment is similar to the embodiment shown in FIG. 7 and described.

Figure 13D:
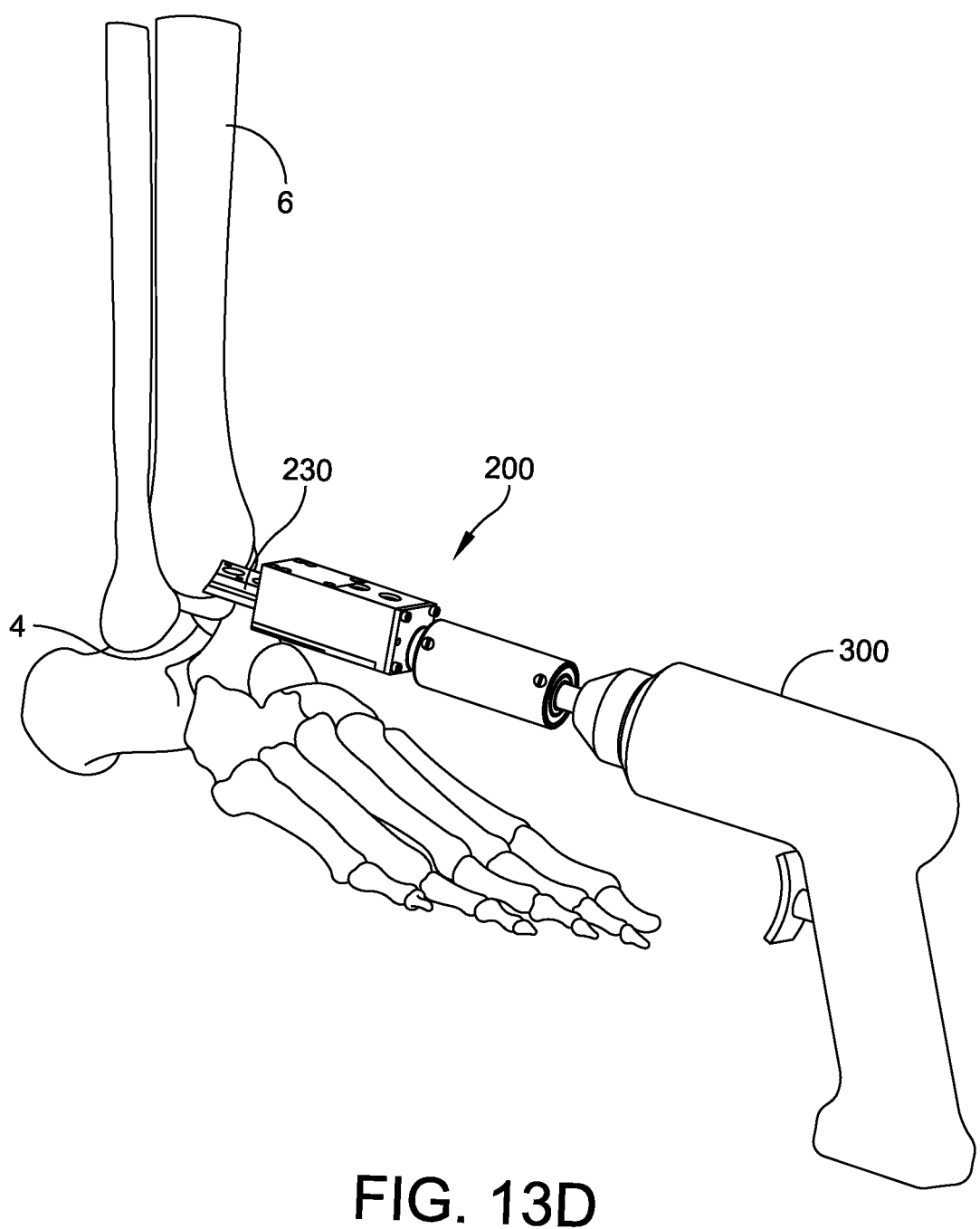
FIG. 13D is an illustration of the inventive power driver of the present disclosure being positioned in the resected joint space of a tibia from the anterior side and oriented with the driver bit toward the talus bone.

The flowchart 4000*a* in FIG. 12G in conjunction with FIG. 13D illustrates an example of an anterior approach method of preparing the proximal end of a talus for receiving a talar implant according to an embodiment. The method comprises resecting the distal end of the tibia and, if necessary, the proximal end of the talus forming a resected joint space 22, where the joint space comprises a tibial resection surface at the distal end of the tibia and a talar resection surface at the proximal end of the talus and the joint space 22 is open at the anterior side, see step 4010. Then, the power driver adapter 200 equipped with the cutting tool bit 500 is positioned into the joint space 22 from the anterior side, where the cutting tool bit 500 is aimed toward the talus, see step 4020. Next, the power driver unit 300 is turned on driving the cutting tool bit 500 to cut into the talar resection surface and form a void extending into the talus for receiving a tarlar stem and/or augment for a talar implant, see step 4030.

Figure 12H:
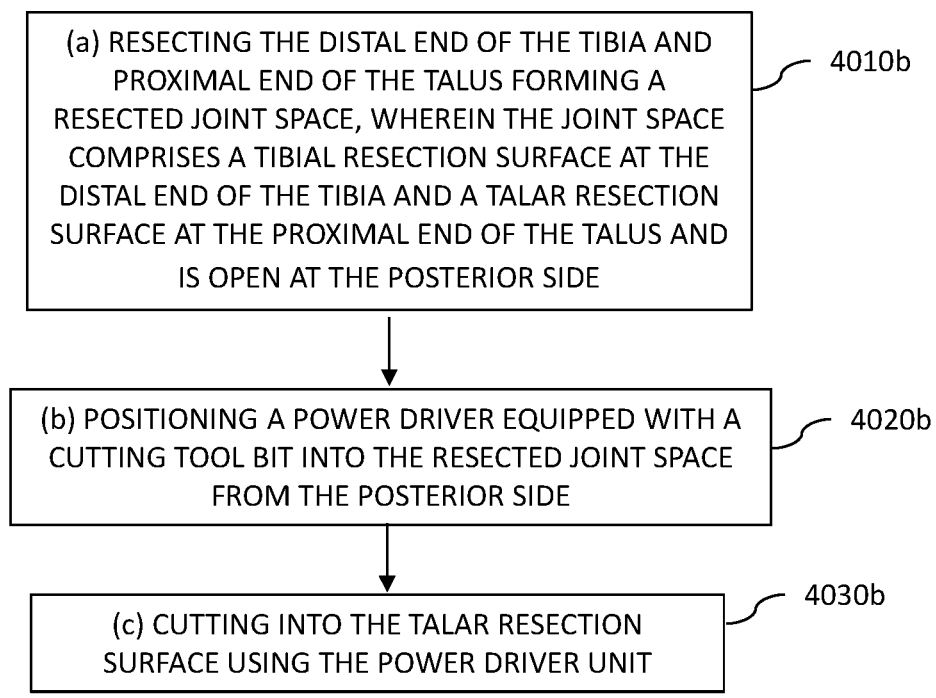
Figure 12:
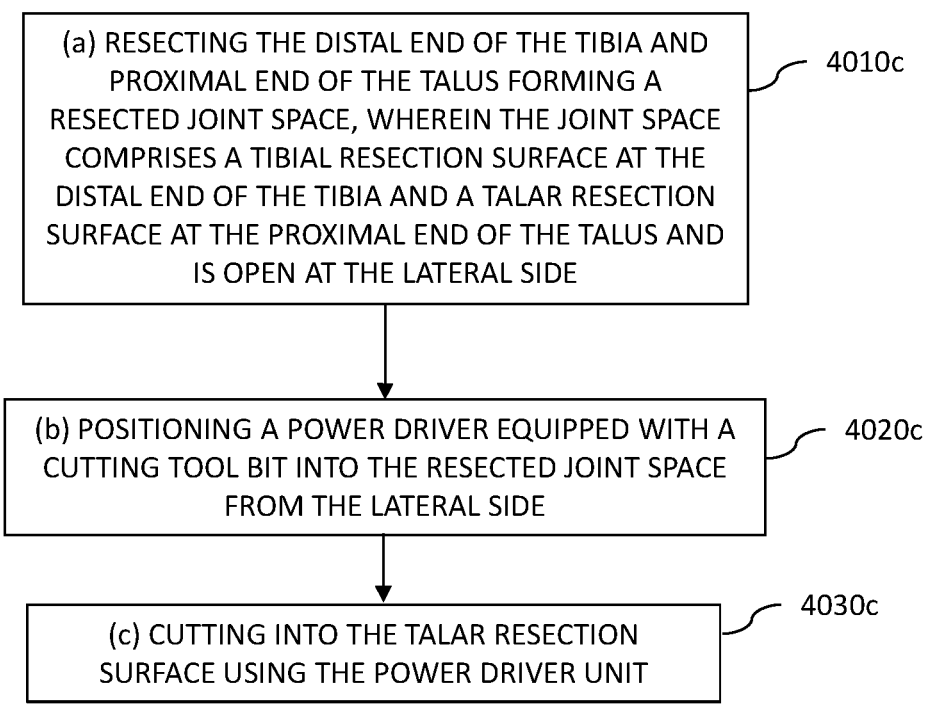

The flowchart 4000*b* in FIG. 12H illustrates an example of a posterior approach method of preparing the proximal end of a talus for receiving a talar implant according to an embodiment. The method comprises resecting the distal end of the tibia and, if necessary, the proximal end of the talus forming a resected joint space 22, where the joint space comprises a tibial resection surface at the distal end of the tibia and a talar resection surface at the proximal end of the talus and the joint space 22 is open at the posterior side, see step 4010*b*. Then, the power driver adapter 200 equipped with the cutting tool bit 500 is positioned into the joint space 22 from the posterior side, where the cutting tool bit 500 is aimed toward the talus, see step 4020*b*. Next, the power driver unit 300 is turned on driving the cutting tool bit 500 to cut into the talar resection surface and form a void extending into the talus for receiving a talar stem and/or augment for a talar implant, see step 4030*b*.

The flowchart 4000*c* in FIG. 12I illustrates an example of a lateral approach method of preparing the proximal end of a talus for receiving a talar implant according to an embodiment. The method comprises resecting the distal end of the tibia and, if necessary, the proximal end of the talus forming a resected joint space 22, where the joint space comprises a tibial resection surface at the distal end of the tibia and a talar resection surface at the proximal end of the talus and the joint space 22 is open at the lateral side, see step 4010*c*. Then, the power driver adapter 200 equipped with the cutting tool bit 500 is positioned into the joint space 22 from the lateral side, where the cutting tool bit 500 is aimed toward the talus, see step 4020*c*. Next, the power driver unit 300 is turned on driving the cutting tool bit 500 to cut into the talar resection surface and form a void extending into the talus for receiving a talar stem and/or augment for a talar implant, see step 4030*c*.

In the various embodiments of the methods described herein, the power driver adapter 200 equipped with the cutting tool bit 500 can be positioned into that ankle joint space between the tibia and the talus before any resection cuts of the tibia or the talus are made. In such examples, an appropriately configured guide assembly jig (not shown) can be inserted into the joint between the tibia and the talus, then guide and position the cutting tool bit end of the power driver adapter 200 between the tibia and the talus before the resection cuts are made to the distal end of the tibia or the proximal end of the talus.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. A surgical instrument kit comprising: a power driver adapter configured for cutting into an intramedullary canal of a tibia, the power driver adapter comprising: an elongated body having a driving end, a cutting tool bit receiving end, and a longitudinal axis; wherein the driving end having a drive shaft coaxially located with the longitudinal axis and configured to mate with a power delivering unit that rotates the drive shaft coaxially about the longitudinal axis; wherein the cutting tool bit receiving end comprises a cutting tool bit receiving base that is configured for engaging with a cutting tool bit and rotates the cutting tool bit for cutting action, wherein the cutting tool bit receiving base rotates with a rotational axis that is orthogonal to the longitudinal axis of the elongated body; wherein the elongated body comprises a series of gears connecting the drive shaft to the cutting tool bit receiving end; wherein the series of gears are configured in an arrangement that converts a coaxial rotation of the drive shaft to a rotation of the cutting tool bit receiving base; and a guide assembly comprising: a guide portion configured for attaching to a resected surface at a distal end of the tibia, wherein the guide portion comprises a hole for receiving and allowing the cutting tool bit to extend therethrough; and a guide head portion extending in proximal direction from the guide portion and configured for attaching to the anterior side of the tibia, wherein the cutting tool bit receiving end of the elongated body is configured to translate linearly in a direction that is coaxial to the rotational axis of the cutting tool bit and orthogonal to the longitudinal axis.

2. The surgical instrument kit of claim 1, wherein the cutting tool bit is a reamer bit.

3. The surgical instrument kit of claim 1, wherein the cutting tool bit receiving base is configured to engage threads of the cutting tool bit.

4. The surgical instrument kit of claim 1, wherein the cutting tool bit comprises a threaded base stem and the cutting tool bit receiving base includes a threaded hole for engaging with the cutting tool bit.

5. The surgical instrument kit of claim 1, wherein the elongated body of the power driver adapter comprises one or more alignment posts, and the guide head portion comprises one or more corresponding alignment slots that are configured for receiving the alignment posts for establishing an alignment relationship between the power driver and the guide assembly.

6. The surgical instrument kit of claim 1, wherein the guide head portion further comprising one or more holes extending therethrough for receiving guide wires or fixation pins for securing the guide assembly to the tibia.

7. The surgical instrument kit of claim 1, wherein the series of gears comprises a bevel gear arrangement.

8. The surgical instrument kit of claim 1, wherein the series of gears comprises a spur gear arrangement.

9. The surgical instrument kit of claim 1, further comprising one or more cutting tool bits.

10. The surgical instrument kit of claim 1, wherein the series of gears comprises a helical thread arrangement that translates the cutting tool bit receiving end linearly.

* * * * *